US011759524B2

(12) United States Patent
Bayir et al.

(10) Patent No.: US 11,759,524 B2
(45) Date of Patent: *Sep. 19, 2023

(54) MITOCHONDRIALLY TARGETED PARP INHIBITOR, AND USES THEREOF

(71) Applicant: University of Pittsburgh—Of the Commonwealth System of Higher Education, Pittsburgh, PA (US)

(72) Inventors: Hulya Bayir, Pittsburgh, PA (US); Peter Wipf, Pittsburgh, PA (US); Tanja Krainz, Pittsburgh, PA (US); Robert Clark, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/403,182

(22) Filed: Aug. 16, 2021

(65) Prior Publication Data

US 2021/0379191 A1    Dec. 9, 2021

Related U.S. Application Data

(63) Continuation of application No. 16/340,237, filed as application No. PCT/US2017/056503 on Oct. 13, 2017, now Pat. No. 11,090,389.

(60) Provisional application No. 62/407,639, filed on Oct. 13, 2016.

(51) Int. Cl.
| | |
|---|---|
| *A61K 47/64* | (2017.01) |
| *A61P 39/00* | (2006.01) |
| *A61K 31/4184* | (2006.01) |
| *A61K 45/06* | (2006.01) |

(52) U.S. Cl.
CPC .......... *A61K 47/64* (2017.08); *A61K 31/4184* (2013.01); *A61K 45/06* (2013.01); *A61P 39/00* (2018.01)

(58) Field of Classification Search
None
See application file for complete search history.

(56) References Cited

U.S. PATENT DOCUMENTS

| | | |
|---|---|---|
| 5,380,758 A | 1/1995 | Stamler et al. |
| 5,763,625 A | 6/1998 | Boothman et al. |
| 5,824,700 A | 10/1998 | Frydman et al. |
| 5,908,756 A | 6/1999 | Snyder et al. |
| 5,969,163 A | 10/1999 | Frydman et al. |
| 6,075,121 A | 6/2000 | Simon et al. |
| 6,331,532 B1 | 12/2001 | Murphy et al. |
| 6,656,498 B1 | 12/2003 | Gao |
| 6,696,038 B1 | 2/2004 | Mahato et al. |
| 6,749,863 B1 | 6/2004 | Chang et al. |
| 7,528,174 B2 | 5/2009 | Wipf et al. |
| 7,718,603 B1 | 5/2010 | Wipf et al. |
| 7,790,765 B2 | 9/2010 | Bartis et al. |
| 8,068,459 B2 | 11/2011 | Kravtsov et al. |
| 8,288,551 B2 | 10/2012 | Wipf et al. |
| 8,609,850 B2 | 12/2013 | Wipf et al. |
| 8,937,086 B2 | 1/2015 | Niedernhofer et al. |
| 9,006,186 B2 | 4/2015 | Wipf et al. |
| 2005/0107366 A1 | 5/2005 | Carney et al. |
| 2005/0169904 A1 | 8/2005 | Payne |
| 2005/0245487 A1 | 11/2005 | Murphy et al. |
| 2007/0161544 A1 | 7/2007 | Wipf et al. |
| 2007/0161573 A1 | 7/2007 | Wipf et al. |
| 2008/0153748 A1 | 6/2008 | Jaynes |
| 2009/0028952 A1 | 1/2009 | Bartis et al. |
| 2009/0042808 A1 | 2/2009 | Fink et al. |
| 2010/0035869 A1 | 2/2010 | Wipf et al. |
| 2011/0039792 A1 | 2/2011 | Wipf et al. |
| 2011/0172214 A1 | 7/2011 | Wipf et al. |
| 2012/0004263 A1 | 1/2012 | Niedernhofer |
| 2014/0018317 A1 | 1/2014 | Wipf et al. |
| 2016/0022825 A1 | 1/2016 | Dhar et al. |

FOREIGN PATENT DOCUMENTS

| | | | |
|---|---|---|---|
| WO | 2010009327 A1 | 1/2010 | |
| WO | 2010009389 A1 | 1/2010 | |
| WO | 2010009405 A2 | 1/2010 | |
| WO | 2012112851 A2 | 8/2012 | |
| WO | 2013123298 A1 | 8/2013 | |

OTHER PUBLICATIONS

Wipf et al., "Convergent Approach to (E)-Alkene and Cyclopropane Peptide Isosteres", Organic Letters, 2005, pp. 103-106, vol. 7, No. 1.
Wipf et al., "Three-Component Synthesis of a, β-Cyclopropyi-γ-Amino Adds", Organic Letters, 2005, pp. 1137-1140, vol. 7, No. 6.
Wipf et al., "Synthesis of Chemoreversible Prodrugs of ara-C with Variable Time-Release Profiles. Biological Evaluation of Their Apoptotic Activity", Bioorganic & Medicinal Chemistry, 1996, pp. 1585-1596, vol. 4, No. 10.
Wipf et al., "Imine Additions of Internal Alkynes for the Synthesis of Trisubstituted (E)-Alkene and Cyclopropane Peptide Isosteres", Adv. Synth. Catal., 2005, pp. 1605-1613, vol. 347.
Wipf et al., "Methyl and (Trifluoromethyl)alkene Peptide Isosteres: Synthesis and Evaluation of Their Potential as β-Turn Promoters and Peptide Mimetics", J. Org Chem., 1998, pp. 6088-6089, vol. 63, No. 18.
Wipf et al., "Mitochondrial Targeting of Selective Electron Scavengers: Synthesis and Biological Analysis of Hemigramicidin-TEMPO Conjugates", J. Am. Chem. Soc., 2004, pp. 12460-12461, vol. 127.
Wondrak, "Redox-Directed Cancer Therapeutics: Molecular Mechanisms and Opportunities", Antioxidants & Redox Signaling, 2009, pp. 3013-3069, vol. 11, No. 12.
Wood et al., "Neurotoxicity of reactive aldehydes: the concept of "aldehyde load" as demonstrated by neuroprotection with hydroxylamines", Brain Research, 2006, pp. 190-199, vol. 1095, No. 1.

(Continued)

*Primary Examiner* — Thomas S Heard
(74) *Attorney, Agent, or Firm* — The Webb Law Firm

(57) ABSTRACT

A mitochondrial-targeted PARP inhibitor is provided herein, as well as methods of making and using the mitochondrial-targeted PARP inhibitor.

8 Claims, 11 Drawing Sheets

(56) References Cited

OTHER PUBLICATIONS

Wu et al., "Metabolic Reprogramming of Human Cells in Response to Oxidative Stress: Implica-tions in the Pathophysiology and Therapy of Mitochondrial Diseases", Current Pharmaceutical Design, 2014, pp. 5510-5526, vol. 20.

Xiao et al., "Electrostatic versus Steric Effects in Peptidomimicry: Synthesis and Secondary Structure Analysis of Gramicidin S Analogues with (E)-Alkene Peptide Isosteres", J. Am. Chem. Soc., 2005, pp. 5742-5743, vol. 127, No. 16.

Xun et al., "Targeting of XJB-5-131 to mitochondria suppresses oxidative DNA damage and motor decline in a mouse model of Huntington's disease", Cell Rep., 2012, pp. 1137-1142, vol. 2, No. 5.

Yamamoto et al., "Anti-tumor promoting action of phthalic acid mono-n-butyl ester cupric salt, a biomimetic superoxide dismutase", Carcinogenesis, 1990, pp. 749-754, vol. 11, No. 5.

Yang et al., "Ethyl pyruvate modulates inflammatory gene expression in mice subjected to hemorrhagic shock", Am J Physiol Gastrointest Liver Physiol, 2002, pp. G212-G221, vol. 283, No. 1.

Yousif et al., "Mitochondria-Penelrating Peptides: Sequence Effects and Model Cargo Transport," ChemBioChem, 2009, pp. 2081-2088, vol. 10.

Yousif et al., "Targeting Mitochondria with Organelle-Specific Compounds: Strategies and Applications", ChemBioChem, 2009, pp. 1939-1950, vol. 10.

Zhang et al., "Induction of mitochondrial dysfunction as a strategy for targeting tumour cells in metabolically compromised microenvironments", Nature Communications, 2014, pp. 1-14, vol. 5, No. 3295.

Zhao et al., "Cell-permeable Peptide Antioxidants Targeted to Inner Mitochondrial Membrane inhibit Mitochondrial Swelling, Oxidative Cell Death, and Reperfusion Injury", The Journal of Biological Chemistry, 2004, pp. 34682-34690, vol. 279, No. 33.

Zhou et al., "Design of iron chelators with therapeutic application", Dalton Transactions, 2012, pp. 6371-6389, vol. 41.

Delude et al., "Novel Nitroxide-Gramicidin Conjugates Target Mitochondria ROS Production and Decrease Inflammation", Society of Critical Care Medicine's 37th Critical Care Congress Abstracts, Crit Care Med., 2007, 35 (12 Supple): A18, (Abstract 72).

Krishna et al., "Do nitroxide antioxidants act as scavengers of O2—or as SOD mimics?", J Biol Chem, 1996,18;271(42), pp. 26026-26031.

Beaumont et al., "Design of Ester Prodrugs to Enhance Oral Absorption of Poorly Permeable Compounds: Challenges to the Discovery Scientist", Current Drug Metabolism, 2003, pp. 461-485, vol. 4.

Ettmayer, P. et al., "Lessons Learned from Marketed and Investigational Prodrugs", J. Med. Chem., 2004, pp. 2393-2404, vol. 47, No. 10.

Han, H.-K.,"Targeted Prodrug Design to Optimize Drug Delivery", AAPS Pharmsci, 2000, pp. 1-11, vol. 2, No. 1.

Muller, C.E. et al., "Prodrug Approaches for Enhancing the Bioavailability of Drugs with Low Solubility" Chemistry & Biodiversity, 2009, pp. 2071-2083, vol. 6.

Singh, Y. et al., "Recent Trends in Targeted Anticancer Prodrug and Conjugate", Curr Med Chem, 2008, pp. 1802-1826, vol. 15, No. 18.

Testa, B., "Prodrug research: futile or fertile?", Biochem. Pharm., 2004, pp. 2097-2106, vol. 68, No. 11.

Nakane et al., "Novel Potent and Selective Inhibitors of Inducible Nitric Oxide Synthase", Molecular Pharmacology, 1995, pp. 831-834, vol. 47.

Neuzil et al., "Classification of mitocans, anti-cancer drugs acting on mitochondria," Mitochondrion, 2013, pp. 199-208, vol. 13.

Newmeyer et al.,"Mitochondria: Releasing Power for Life Review and Unleashing the Machineries of Death," Cell, 2003, pp. 481-490, vol. 112.

Niccolai et al., "An Investigation of the Mechanisms of Nitroxide-Induced Proton Relaxation Enhancements in Biopolymers", J. Phys. Chem., 1984, pp. 5689-5692, vol. 88.

Nicolas et al., "Molecular strategies in biological evolution of antimicrobial peptides", Peptides, 2003, pp. 1669-1680, vol. 24, No. 11.

Nishiyama et al., "Systemic and Regional Hemodynamic Responses to Tempol in Angiotensin II-Infused Hypertensive Rats", Hypertension, 2001, pp. 77-83, vol. 37.

O'Connor et al., "Powders," Remington: The Science and Practice of Pharmacy, 2005, Lippincott, 21st Ed., pp. 702-928, Williams and Williams, Philadelphia.

Olcott et al., "A Salen-Manganese Catalytic Free Radical Scavenger Inhibits Type 1 Diabetes and Islet Allograft Rejection", Diabetes, 2004, pp. 2574-2580, vol. 53, No. 10.

Olszewska et al., "Critical Review Mitochondria as a Pharmacological Target: Magnum Overview", IUBMB Life, 2013, pp. 273-281, vol. 65, No. 3.

Ott et al., "Mitochondria, oxidative stress and cell death", Apoptosis, 2007, pp. 913-922, vol. 12.

Pantano et al., "Redox-Sensitive Kinases of the Nuclear Factor-kappaB Signaling Pathway", Antioxidants & Redox Signaling, 2006, pp. 1791-1806, vol. 8, Nos. 9 & 10.

Park et al., "β-Lapachone-induced reactive oxygen species (ROS) generation mediates autophagic cell death in glioma U87 MG cells", Chemico-Biological Interactions, 2011, pp. 37-44, vol. 189.

Park et al., "β-Lapachone induces programmed necrosis through the RIP1-PARP-AIF-dependent pathway in human hepatocellular carcinoma SK-Hep1 cells", Cell Death and Disease, 2014, pp. 1-10, vol. 5.

Pathak et al., "Mito-DCA: A Mitochondria Targeted Molecular Scaffold for Efficacious Delivery of Metabolic Modulator Dichlaroacetate", ACS Chemical Biology, 2014, pp. 1178-1187, vol. 9.

Payne et al., "Conformer Profiles and Biological Activities of Peptides", Current Organic Chemistry, 2002, pp. 1221-1246, vol. 6.

Pieper et al., "Protective Mechanisms of a Metalloporphyrinic Peroxynitrite Decomposition Catalyst, WW85, in Rat Cardiac Transplants", The Journal of Pharmacology and Experimental Therapeutics, 2005, pp. 53-60, vol. 314, No. 1.

Pink el al., "NAd(P)H:Quinone Oxidoreductase Activity is the Principal Determinant of β-Lapachone Cytotoxicity", The Journal of Biological Chemistry, 2000, pp. 5416-5424, vol. 275, No. 8.

Planchon et al., "β-Lapachone-mediated Apoptosis in Human Promyelocytic Leukemia (HL-60) and Human Prostate Cancer Cells: A p53-independent Response," Cancer Res., 1995, pp. 3706-3711, vol. 55, No. 17.

Porter et al., "Mimicry of Host-Defense Peptides by Unnatural Oligomers: Antimicrobial β-peptides", J. Am. Chem. Soc., 2002, pp. 7324-7330, vol. 124, No. 25.

Qian et al., "Alterations in bioenergetics due to changes in mitochondrial DNA copy number", Methods, 2010, pp. 452-457, vol. 51.

Raguse et al., "Structure-Activity Studies of 14-Helical Antimicrobial β-Peptides: Probing the Relationship Between Conformational Stability and Antimicrobial Potency", J. Am. Chem. Soc., 2002, pp. 12774-12785, vol. 124, No. 43.

Ray et al., "Reactive oxygen species (ROS) homeostasis and redox regulation in cellular signaling", Cellular Signalling, 2012, pp. 981-990, vol. 24.

Sabharwal et al., "Mitochondrial ROS in cancer initiators, amplifiers or an Achilles' heel?", Nat. Rev. Cancer, 2014, pp.709-721, vol. 14, No. 11.

Salas et al., "Trypanosoma cruzi: Activities of lapachol and a- and β-lapachone derivatives against epimastigote and trypomastigote forms", Bioorganic & Medicinal Chemistry, 2008, pp. 668-674, vol. 16.

Samuni et al., "Nitroxide SOD-mimics: modes of action", Free Radic Res Commun., 1991, pp. 187-194, vols. 12-13, No. 1.

Scaffidi et al., "Release of chromatin protein HMGB1 by necrotic cells triggers inflammation", Nature, 2002, 191-195, vol. 418, No. 6894.

Scharte et al., "Cytokines induce HIF-1 DNA binding and the expression of HIF-1-dependent genes in cultured rat enterocytes", Am J Physiol Gastronintest Liver Physiol., 2002, pp. G373-G384, vol. 284, No. 3.

(56) References Cited

OTHER PUBLICATIONS

Scherz-Shouval et al., "Regulation of autophagy by ROS: physiology and pathology", Trends in Biochemical Sciences, 2011, pp. 30-38, vol. 36, No. 1.
Schnackenberg et al., "Two-Week Administration of Tempol Attenuates Both Hypertension and Renal Excretion of 3-Iso Prostaglandin F2a", Hypertension, 1999, pp. 424-428, vol. 33.
Sena et al., "Physiological Roles of Mitochondrial Reactive Oxygen Species", Molecular Cell, 2012, pp. 158-167, vol. 48.
Sharma et al., "Mitochondrial Alteration: A Major Player in Carcinogenesis", Cell Biology, 2015, pp. 8-16, vol. 3, No. 2-1.
Sheu et al., "Targeting antioxidants to mitochondria: A new therapeutic direction", Biochimica et Biophysica Acta, 2006, pp. 256-265, vol. 1762.
Shidoji et al., "Loss of Molecular Interaction Between Cytochrome c and Cardiolipin Due to Lipid Peroxidation", Biochemical and Biophysical Research Communications, 1999, pp. 343-347, vol. 264, No. 2.
Sholtz et al., "Effect of Gramicidin S and its Derivatives on the Mitochondrial Membrane", FEBS Letters, 1975, pp. 141-144, vol. 58, No. 1.
Skoda et al., "Allylic Amines as Key Building Blocks in the Synthesis of (E)-Alkene Peptide Isosteres", Org Process Res Dev., 2012, pp. 26-34, vol. 16, No. 1.
Sullivan et al., "Mitochondrial reactive oxygen species and cancer", Sullivan and Chandel Cancer & Metabolism, 2014, pp. 1-12, vol. 2, No. 17.
Sun et al., "A Preparative Synthesis of Lapachol and Related Naphthoquinones", Tetrahedron Letters, 1998, pp. 8221-8224, vol. 39.
Szeto, "Mitochondria-Targeted Peptide Antioxidants: Novel Neuroprotective Agents", The AAPS Journal, 2006, pp. E521-E531, vol. 8, No. 3.
Tamaki et al., "CD spectra and cyclization of linear pentapeptides as gramicidin S precursors with a benzyloxycarbonyl group on the side chain of Orn residue", Bull Chem Soc Jpn., 1993, pp. 3113-3115, vol. 66, No. 10.
Thiemermann, "Membrane-permeable radical scavengers (tempol) for shock, ischemia-reperfusion injury and inflammation", Crit. Care Med., 2003, pp. S76-S84, vol. 31, No. 1.
Tomasetti et al., "Redox-active and Redox-silent Compounds: Synergistic Therapeutics in Cancer", Current Medicinal Chemistry, 2015, pp. 552-568, vol. 22.
Trachootham et al., "Targeting cancer cells by ROS-mediated mechanisms: a radical therapeutic approach?", Nature Reviews Drug Discovery, 2009, pp. 579-591, vol. 8.
Tuominen et al., "Phospholipid-Cytochrome c Interaction: Evidence for The Extended Lipid Anchorage", The Journal of Biological Chemistry, 2002, pp. 8822-8826, vol. 277, No. 11.
Uttara et al., "Oxidative Stress and Neurodegenerative Diseases: A Review of Upstream and Downstream Antioxidant Therapeutic Options", Current Neuropharmacology, 2009, pp. 65-74, vol. 7.
Wade et al., "Antibiotic properties of novel synthetic temporin a analogs and a cecropin A-temporin a hybrid peptide", Protein and Peptide Letters, 2002, pp. 533-543, vol. 9, No. 6.
Wallace, "Mitochondria and cancer", Nat Rev Cancer, 2012, pp. 685-698, vol. 12, No. 10.
Wang et al., "Activation of the NRF2 Signaling Pathway by Copper-Mediated Redox Cycling of Para- and Ortho-Hydroquinones", Chemistry & Biology, 2010, pp. 75-85, vol. 17.
Wattanasirichaigoon et al., "Effect of mesenteric ischemia and reperfusion or hemorrhagic shock on intestinal mucosal permeability and ATP content in rats", Shock, 1999, pp. 127-133, vol. 12, No. 2.
Weinberg et al., "Targeting mitochondria metabolism for cancer therapy," Nat Chem Biol, 2015, pp. 9-15, vol. 11, No. 1.
Wellington, "Understanding cancer and the anticancer activities of naphthoquinones—a review", RSC Advances, 2015, pp. 20309-20338, vol. 5.
Huang et al., "Superoxide dismutase as a target for the selective killing of cancer cells", Nature, 2000, pp. 390-395, vol. 407.
Imai et al., "Protection from inactivation of the adenine nucleotide translocator during hypoglycaemia-induced apoptosis by mitochondrial phospholipid hydroperoxide glutathione peroxidase", Biochem J., 2003, pp. 799-809, vol. 871, No. 3.
Itami et al., "Superoxide dismutase mimetic activities of metal complexes of L-2(2-pyridyl)-1-pyrroline-5-carboxylic acid (pyrimine)", Biochem Biophys Res Commun., 1993, pp. 536-541, vol. 197, No. 2.
Iverson et al., "The cardiolipin-cytochrome c interaction and the mitochondrial regulation of apoptosis", Arch Biochem Biophys., 2004, pp. 37-46, vol. 423, No. 1.
Jackel et al., "Fluorine in Peptide Design and Protein Engineering", Eur. J. Org. Chem., 2005, pp. 4483-4503.
Jean et al., "Molecular Vehicles for Mitochondrial Chemical Biology and Drug Delivery," ACS Chemical Biology, 2014, pp. 323-333, vol. 9.
Jelokhani-Niaraki et al., "Diastereoisomeric analogues of gramicidin S: structure, biological activity and interaction with lipid bilayers", Biochem J., 2000, pp. 747-755, vol. 349.
Ji et al., "Global lipidomics identifies cardiolipin oxidation as a mitochondrial target for redox therapy of acute brain injury", Nat. Neurosci., 2012, pp. 1407-1413, vol. 15, No. 10.
Ji et al., "Deciphering of mitochondrial cardiolipin oxidative signaling in cerebral ischemia-reperfusion," Journal of Cerebral Blood Flow & Metabolism, 2015, pp. 319-328, vol. 35.
Jiang et al., "Structural Requirements for Optimized Delivery, Inhibition of Oxidative Stress, and Antiapoptotic Activity of Targeted Nitroxides", The Journal of Pharmacology and Experimental Therapeutics, 2007, pp. 1050-1060, vol. 320, No. 3.
Jian-Jun et al., "Phenyl-a-tert-Butyl Nitron Reverses Mitochondrial Decay in Acute Chagas' Disease", The American Journal of Pathology, 2006, pp. 1953-1964, vol. 169, No. 6.
Jordan, "Tamoxifen: A Most Unlikely Pioneering Medicine", Nature Reviews, 2003, pp. 205-213, vol. 2.
Kagan et al., "A role for oxidative stress in apoptosis: oxidation and externalization of phosphatidylserine is required for macrophage clearance of cells undergoing Fas-medicated apoptosis", The Journal of Immunology, 2002, pp. 487-499, vol. 169, No. 1.
Kagan et al., "Cytochrome c acts as a cardiolipin oxygenase required for release of proapoptotic factors", Nature Chemical Biology, 2005, pp. 223-232, vol. 1, No. 4.
Kagan et al., "Mitochondrial targeting of electron scavenging antioxidants: Regulation of selective oxidation vs random chain reactions", Adv Drug Deliv Rev., 2009, pp. 1375-1385, vol. 61, No. 14.
Kagan et al.. "Oxidative lipidomics of apoptosis: redox catalytic interactions of cytochrome c with cardiolipin and phosphatidylserine", Free Radical Biology and Medicine, 2004, pp. 1963-1985, vol. 37, No. 12.
Kamata et al., "Topical Review Redox Regulation of Cellular Signalling," Cell. Signal., 1999, pp. 1-14, vol. 11, No. 1.
Kanai et al., "Mitochondrial targeting of radioprotectants using peptidyl conjugates," Org Biomol Chem., 2007, pp. 1-8, vol. 5, No. 2.
Kanai et al., "Identification of a neuronal nitric oxide synthase in isolated cardiac mitochondria using electrochemical detection", Proc Natl Acad Sci U S A, 2001, pp. 14126-14131, vol. 98, No. 24.
Kanai et al., "Manganese superoxide dismutase gene therapy protects against irradiation-induced cystitis", Am J Physiol Renal Physiol, 2002, F1304-F1312, vol. 283, No. 6.
Kanai et al., "Function and regulation of mitochondrially produced nitric oxide in cardiomyocytes", Am J Physiol Heart Circ Physiol, 2004, pp. H11-H12, vol. 286, No. 1.
Kanai et al., "Differing roles of mitochondrial nitric oxide synthase in cardiomyocytes and urothelial cells", Am J Physiol Heart Circ Physiol, 2004, pp. H13-H21, vol. 286, No. 1.
Keinan et al., "Computational design, synthesis and biological evaluation of para-quinone-based inhibitors for redox regulation of the dual specificity phosphatase Cdc25B", Org Biomol Chem., 2008, pp. 3256-3263, vol. 6, No. 18.

(56) References Cited

OTHER PUBLICATIONS

Kelso et al, "Selective Targeting of a Redox-active Ubiquinone to Mitochondria within Cells: Antioxidant and Antiapoptotic Properties", J Biol Chem, 2001, pp. 4588-4596, vol. 276, No. 7.

Kentner et al., "Early Antioxidant Therapy with Tempol During Hemorrhagic Shock Increases Survival in Rats", J Trauma, 2002, pp. 968-977, vol. 53, No. 5.

Kondejewski et al., "Gramicidin S is active against both gram-positive and gram-negative bacteria", Int J Pept Protein Res, 1996, pp. 460-466, vol. 47, No. 6.

Konorev et al., "Cell-permeable superoxide dismutase and glutathione peroxidase mimetics afford superior protection against doxorubicin-induced cardiotoxicity: the role of reactive oxygen and nitrogen intermediates", Arch Biochem Biophys, 1999, pp. 421-428, vol. 368, No. 2.

Kung et al., "The Chemotheraputic Effects of Lapacho Tree Extract: β-Lapachone," Chemotherapy, 2014, pp. 1-5, vol. 3, No. 2.

Lacza et al., "Mitochondrial NO and reactive nitrogen species production: Does mtNOS exist?", Nitric Oxide, 2006, pp. 162-168, No. 14.

Lee et al., "Structure-Activity Relationships of de novo Designed Cyclic Antimicrobial Peptides Based on Gramicidin S", Biopolymers, 2003, pp. 28-48, vol. 71, No. 1.

Li et al., "Release of Mitochondrial Cytochrome C in Both Apoptosis and Necrosis Induced by β-Lapachone in Human Carcinoma Cells," Molecular Medicine, 1999, pp. 232-239, vol. 5.

Li et al., "Potent Induction of Apoptosis by β-Lapachone in Human Multiple Myeloma Cell Lines and Patient Cells," Molecular Medicine, 2000, pp. 1008-1015, vol. 6, No. 12.

Li et al., "Mechanistic studies of cancer cell mitochondria- and NQO1-mediated redox activation of beta-lapachone, a potentially novel anticancer agent," Toxicology and Applied Pharmacology, 2014, pp. 285-293, vol. 281.

Liaw et al., "Effects of a Membrane-Permeable Radical Scavenger, Tempol, on Intraperitoneal Sepsis-Induced Organ Injury in Rats", Shock, 2005, pp. 88-96, vol. 23, No. 1.

Lin et al., "Superoxide Dismutase Inhibits the Expression of Vascular Cell Adhesion Molecule-1 and Intracellular Cell Adhesion Molecule-1 Induced by Tumor Necrosis Factor-a in Human Endothelial Cells Through the JNK/p38 Pathways", Arterioscler Thromb Vasc Biol, 2005, pp. 334-340, vol. 25, No. 2.

Lin et al., "Mitochondrial dysfunction and oxidative stress in neurodegenerative diseases," Nature, 2006, pp. 787-795, vol. 443.

Lirk et al., "Inducible Nitric Oxide Synthase—Time for Reappraisal", Current Drug Targets—Inflammation & Allergy, 2002, pp. 89-108, vol. 1.

Liu et al., "Redox-Dependent Transcriptional Regulation", Circ Res, 2005, pp. 967-974, vol. 97, No. 10.

Ma et al., "Mitochondrial targeted b-lapachone induces mitochondrial dysfunction and catastrophic vacuolization in cancer cells," Bioorganic & Medicinal Chemistry Letters, 2015, pp. 4828-4-833, vol. 25.

Macias et al., "Treatment With a Novel Hemigramicidin-Tempo Conjugate Prolongs Survival in a Rat Model of Lethal Hemorrhagic Shock", Ann Surg, 2007, pp. 305-314, vol. 245, No. 2.

Macias et al., "A Novel Hermigramicidin-Tempo Conjugate Has Anti-Inflammatory Effect In Vitro and In Vivo", Society of Critical Care Medicine's 36th Critical Congress Abstracts, Crit Care Med, 2006, p. 30, vol. 34, No. 12.

McDonald et al., "Tempol reduces infarct size in rodent models of regional myocardial ischemia and reperfusion", Free Radical Biology and Medicine, 1999, pp. 493-503, vol. 27, Nos. 5/6.

Mitchell et al., "Radiation, Radicals, and Images", Annals New York Academy of Sciences, 2000, pp. 28-43, vol. 899.

Modica-Napolitano et al., "Milochondrial dysfunction in cancer", Mitochondrion, 2004, pp. 755-762, vol. 4.

Munoz-Pinedo et al., "Autosis: a new addition to the cell death tower of babel", Cell Death and Disease, 2014, pp. 1-2, vol. 5.

Murphy et al., "How mitochondria produce reactive oxygen species," Biochem. J., 2009, pp. 1-13, vol. 417.

Murphy et al., "Targeting Antioxidants to Mitochondria by Conjugation to Lipophilic Cations," The Annual Review of Pharmacology and Toxicology, 2007, pp. 629-656, vol. 47.

Nagai et al., "Pathophysiological Roles of ASK1-MAP Kinase Signaling Pathways", Journal of Biochemistry and Molecular Biology, 2007, pp. 1-6, vol. 40, No. 1.

Nakajima et al.,"Metabolic Symbiosis in Cancer: Refocusing the Warburg Lens," Molecular Carcinogenesis, 2013, pp. 329-337, vol. 52.

Nakajima et al., "Quantifying Metabolic Heterogeneity in Head and Neck Tumors in Real Time: 2-DG Uptake is Highest in Hypoxic Tumor Regions," PLOS ONE, 2014, pp. 1-12, vol. 9, No. 8.

Abashkin et al., "(salen)MnIII Compounds as Nonpeptidyi Mimics of Catalase. Mechanism-Based Tuning of Catalase Activity: A Theoretical Study", Inorg Chem., 2005, pp. 1425-1432, vol. 44, No. 5.

Adam et al., "The HSP70 Modulator MAL3-101 Inhibits Merkel Cell Carcinoma", PLOS One, 2014, pp. 1-8, vol. 9.

Adam-Vizi et al., "Bioenergetics and the formation of mitochondrial reactive oxygen species", ScienceDirect, 2006, pp. 639-645, vol. 27, No. 12.

Andreyev et al., "Mitochondrial Metabolism of Reactive Oxygen Species", Biochemistry (Moscow), 2005, pp. 200-214, vol. 70, No. 2.

Apostolova et al., "Molecular Strategies for Targeting Antioxidants to Mitochondria: Therapeutic Implications", Antioxidants & Redox Signaling, 2015, pp. 686-729, vol. 22, No. 18.

Baker et al., "Polarized Caco-2 Cells. Effect of Reactive Oxygen Metabolites on Enterocyte Barrier Function", Digestive Diseases and Sciences, 1995, pp. 510-518, vol. 40, No. 3.

Balaban et al., "Mitochondria, Oxidants, and Aging", Cell, 2005, pp. 483-495, vol. 120, No. 4.

Banan et al., "Activation of Delta-Isoform of Potein Kinase C is Required for Oxidant-Induced Disruption of Both the Microtubule Cytoskeleton and Permeability Barrier of Intestinal Epithelia", J Pharmacol Exp Ther., 2002, pp. 17-28, vol. 303, No. 1.

Barnham et al., "Neurodegenerative Diseases and Oxidative Stress", Nature Reviews Drug Discovery, 2004, pp. 205-214, vol. 3.

Batinic-Haberle et al., "New PEG-ylated Mn(III) porphyrins approaching catalytic activity of SOD enzyme", Dalton Transactions, 2006, pp. 617-624.

Berry, "Endosymbiosis and the design of eukaryotic electron transport", Biochimica et Biophysica Acta, 2003, pp. 57-72, vol. 1606, Nos. 1-3.

Bey et al., "An NQ01- and PARP-1-mediated cell death pathway induced in non-small-cell lung cancer cells by b-lapachone", PNAS, 2007, pp. 11832-11837, vol. 104, No. 28.

Bey et al., "Catalase Abrogates b-Lapachone-Induced PARP1 Hyperactivation-Directed Programmed Necrosis in NQO1-Positive Breast Cancers", Molecular Cancer Therapeutics, 2013, pp. 2110-2121, vol. 12, No. 10.

Biasutto et al., "Mitochondrially targeted anti-cancer agents", Mitochondrian, 2010, pp. 670-681, vol. 10.

Bottcher, et al., "A rapid and sensitive sub-micro phosphorous determination," Anal Chim Acta, 1961, pp. 203-204, vol. 24.

Brieger et al., "Reactive oxygen species: from health to disease", Swiss Medical Weekly, 2012, pp. 1-14, vol. 142.

Buttler et al., "Natural products-the future scaffolds for novel antibiotics?", Biochemical Pharmacology, 2006, pp. 919-929, vol. 71, No. 7.

Cairns, "Rude unhinging of the machinery of life: metabolic approaches to hemorrhagic shock", Curr Opin Crit Care, 2001, pp. 437-443, vol. 7, No. 6.

Chamberlain et al., "Targeted Delivery of Doxorubicin to Mitochondria", ACS Chemical Biology, 2013, pp. 1389-1395, vol. 8.

Chen et al., "Oxidative stress in neurodegenerative diseases", Neural Regeneration Research, 2012, pp. 376-385, vol. 7, No. 5.

Clement et al., "Wild-Type Nonneuronal Cells Extend Survival of SOD1 Mutant Motor Neurons in ALS Mice", Science, 2003, pp. 113-117, vol. 302, No. 5642.

Costantini et al., "Mitochondrion as a Novel Target of Anticancer Chemotherapy", Journal of the National Cancer Institute, 2000, pp. 1042-1053, vol. 92, No. 13.

(56) References Cited

OTHER PUBLICATIONS

Curtin, "PARP inhibitors for anticancer therapy", Biochemical Society Transactions, 2014, pp. 82-88, vol. 42, No. 1.

Cuzzocrea et al., "Effects of tempol, a membrane-permeable radical scavenger, in a gerbil model of brain injury", Brain Research, 2000, pp. 96-106, vol. 875.

Dolder et al., "Mitochondrial Creatine Kinase in Contact Sites: Interaction with Porin and Adenine Nucleotide Translocase, Role in Permeability Transition and Sensitivity to Oxidative Damage", Biological Signals and Receptors, 2001, pp. 93-111, vol. 10, Nos. 1-2.

Dorwald, "Side Reactions in Organic Synethsis: A Guide to Successful Synthesis Design", Weinheim: Wiley-VCH, Verlag GmbH & Co. KGaA, 2005, pp. 1-6.

Droge, "Free Radicals in the Physiological Control of Cell Function", Physiol Rev., 2002, pp. 47-95, vol. 82, No. 1.

Edmonds et al., "Design and Synthesis of a Conformationally Restricted Trans Peptide Isostere Based on the Bioactive Conformations of Saquinavir and Nelfinavir", J Org Chem., 2001, pp. 3747-3752, vol. 66, No. 11.

Epperly et al., "Manganese Superoxide Dismutase (SOD2) Inhibits Radiation-Induced Apoptosis by Stabilization of the Mitochondrial Membrane", Radiation Research, 2002, pp. 568-577, No. 157.

Fink, "Reactive oxygen species as mediators of organ dysfunction caused by sepsis, acute respiratory distress syndrome, or hemmorrhagic shock: potential benefits of resuscitation with Ringer's ethyl pyruvate solution", Curr Opin Clin Nutr Metab Care, 2002, pp. 167-174, vol. 5, No. 2.

Fink et al., "Hemigramicidin-TEMPO conjugates: Novel mitochondria-targeted Antioxidants", Crit. Care. Med, 2007, pp. S461-S467, vol. 35, No. 9.

Folch et al., "A Simple Method for the Isolation and Purification of Total Lipides From Animal Tissues", J Biol. Chem., 1957, pp. 497-509, vol. 226.

Frantz et al., "Mitochondria as a target in treatment", National Institute of Health Environ. Mol. Mutagen, 2010, pp. 462-475, vol. 11, No. 25.

Frantz et al., "Synthesis of analogs of the radiation mitigator JP4-039 and visualization of BODIPY derivatives in mitochondria," National Institute of Health Orig. Biomol. Chem., 2013, pp. 4147-4153, vol. 51, No. 5.

Fulda et al., "Targeting mitochondria for cancer therapy", Nature Reviews Drug Discovery, 2010, pp. 447-464, vol. 9.

Gibson et al., "Amino Acid Derived Macrocycles—An Area Driven by Synthesis or Opplication?", Angew Chem Int Ed Engl., 2006, pp. 1364-1377, vol. 45, No. 9.

Gloire et al., "NF-kappaB activation by reactive oxygen species: Fifteen years later", Biochemical Phamiacology, 2006, pp. 1493-1505, vol. 72, No. 11.

Gorrini et al., "Modulation of oxidative stress as an anticancer strategy", Nature Reviews Drug Discovery, 2013, pp. 931-947, vol. 12.

Graves et al., "Point Mutations in c-Myc Uncouple Neoplastic Transformation from Multiple Other Phenotypes in Rat Fibroblasts", PLoS ONE, 2010, pp. 1-10, vol. 5, No. 10.

Graves et al., "Mitochondrial Structure, Function and Dynamics are Temporally Controlled by c-Myc", PLoS ONE, 2012, pp. 1-13, vol. 7, No. 5.

Gruber et al., "Mitochondria-targeted antioxidants and metabolic modulators as pharmacological interventions to slow ageing", Biotechnology Advances, 2013, pp. 563-592, vol. 31.

Guzik et al., "Nitric Oxide and Superoxide in Inflammation and Immune Regulation", Journal of Physiology and Pharmacology, 2003, pp. 469-487, vol. 54, No. 4.

Hahn et al., "Potential Use of Nitroxides in Radiation Oncology", Cancer Research, 1994, pp. 2006s-2010s, vol. 54.

Hahn et al., "Mn(III)-Desferrioxamine Superoxide Dismutase-Mimic: Alternative Modes of Action", Arch. Biochem. Biophy., 1991, pp. 215-219, vol. 288, No. 1.

Hahn et al., "Tempol, a Stable Free Radical, is a Novel Murine Radiation Protector", Cancer Research, 1992, pp. 1750-1753, vol. 52.

Hail et al., "Cancer chemoprevention and mitochondria: Targeting apoptosis in transformed cells via the disruption of mitochondrial bioenergetics/redox state", Mol. Nutr. Food Res , 2009, pp. 49-67, vol. 53.

Han et al., "Proinflammatory cytokines cause NO-dependent and-independent changes in expression and localization of tight junction proteins in intestinal epithelial cells", Shock, 2003, pp. 229-237, vol. 19, No. 3.

He, "Mannopeptimycins, a novel class of glycopeptide antibiotics active against gram-positive bacteria", Appl Microbiol Biotechnol., 2005, pp. 444-452, vol. 67, No. 4.

Ho et al., "Importance of glycolysis and oxidative phosphorylation in advanced melanoma," Molecular Cancer, 2012, pp. 1-13, vol. 11, No. 76.

Hoye et al., "Targeting Mitochondria," Accounts of Chemical Research, 2008, pp. 87-97, vol. 41, No. 1.

MITOCHONDRIALLY TARGETED PARP INHIBITOR, AND USES THEREOF

CROSS-REFERENCE TO RELATED APPLICATION

This application is a continuation of U.S. patent application Ser. No. 16/340,237 filed Apr. 8, 2019, which is a United States National Phase of International Application No. PCT/US2017/056503 filed Oct. 13, 2017, which claims the benefit of U.S. Patent Application No. 62/407,639 filed Oct. 13, 2016, each of which is incorporated herein by reference in its entirety.

Poly(ADP-Ribose) Polymerase (PARP) is a family of enzymes involved in DNA repair, genome stability, cellular energy metabolism and cell division. Poly(ADP-ribose) polymerases (PARP) are abundant cellular enzymes, with PARP-1 being the most well characterized PARP family member. PARP enzymes build poly(ADP-ribose) polymers (PADPRp) onto target proteins including histones and PARP-1 itself, converting $NAD_+$ to ADP-ribose and nicotinamide while consuming cellular $NAD_+$ stores in the process. PARP-1 is activated by DNA damage and plays a key role in genomic DNA repair, reflected by the fact that it is the second most abundant protein in the cell's nucleus. However, over-activation of PARP-1 can result in critical depletion of cellular $NAD_+$ and initiation of mitochondrial-triggered cell death cascades, leading the scientific field to coin the phrase "suicide theory of PARP activation" (Szabo et al. Trends Pharmacol Sci 1998; 19:287-98) and the term "PARthanatosis" (Andrabi et al. Ann N Y Acad Sci 2008; 1147:233-41), respectively, to characterize PARP-mediated mechanisms of cell death.

Poly(ADP-ribosyl)ation (PARylation) plays a central role in cellular and molecular processes including DNA damage detection and repair, transcription, and the maintenance of genomic integrity. The currently-identified 17 members of the poly(ADP-ribose) polymerase (PARP) family induce the cleavage of $NAD^+$ into nicotinamide and ADP-ribose moieties and mediate their polymerization on target proteins, with links to cellular redox homeostasis, inflammatory, and metabolic networks. While there are broader therapeutic implications for synthetic PARP modulators, poly(ADP-ribose) polymerase-1 (PARP-1) inhibitors have become a hot topic in cancer research since the regulatory approval of olaparib for patients with BRCA1/2 mutant ovarian cancer. PARP-1 binds to nuclear DNA single-strand break (SSBs) sites and recruits repair proteins to the DNA, subsequently dissociating itself from the SSB. The most potent small-molecule inhibitors, rather than just off-setting PARP-1's enzymatic activity, trap it at the SSB site and stabilize PARP-DNA complexes, ultimately causing DNA double-strand breaks that require more complex repair mechanisms.

DNA damage induced by irradiation or oxidative stress leads to over-activation of PARP-1 and induces depletion of cellular $NAD^+$ and ATP levels, leading to cell dysfunction and necrotic cell death. A primary location of $NAD^+$ is in mitochondria, where it is utilized for oxidative phosphorylation. Furthermore, mitochondrial DNA (mtDNA) is constantly being exposed to damaging species such as reactive oxygen and nitrogen species and is efficiently repaired through at least a subset of the species involved in nuclear DNA repair, including PARP-1. In addition to some cancers being exquisitely susceptible to $NAD^+$ depletion over-activation of PARP-1 and $NAD^+$ depletion has been linked to the pathogenesis of central nervous system (CNS) disorders, including ischemia, traumatic brain injury (TBI), neuroinflammation, and neurodegenerative diseases such as Alzheimer's and Parkinson's diseases and chronic traumatic encephalopathy, which have a pronounced mitochondrial component.

It is a widely held belief that PARP activation within cell nuclei accounts for the entirety of PARP-mediated cell death. As such, all PARP inhibitors developed to date target nuclear PARP activation. Disappointingly, despite numerous promising pre-clinical studies dating back to the 1990's targeting nuclear PARP overactivation to prevent cell death, there are no successful clinical applications using PARP inhibitors as mitigators of cell death. Not only that, but PARP inhibitors are being evaluated in cancer trials to enhance tumoricidal activity of DNA damaging chemotherapeutic agents by preventing DNA repair in cancer cells.

Inhibition of PARP-1, a well-characterized member of this family, has been explored as a strategy for enhancing anti-cancer activity of existing drugs and for developing new drugs. Recently unique enzymatic properties and biological functions of PARP-2 and PARP-3 have been discovered, further expanding the utility of PARP as a target for cancer pharmacotherapy. PARP inhibitors in Phase I and Phase II clinical trials, used alone or in combination with known anticancer agents include Olaparib (Ola), Veliparib (Veli) and Rucaparib (Ruca). Prolonged exposure to Ola and Veli leads to resistant cancer cells, primarily through restoration of the homologous recombination (HR) pathway, overexpression of the P-glycoprotein efflux pump or modulation of PARP expression. Some resistant cancer cells continue to respond to platinum based drugs, encouraging further development of PARP inhibitors for cancer treatment. Furthermore, inhibition of mitochondrial PARP has been shown to sensitize malignant, but not non-malignant, cells to anticancer drugs. Thus, it is possible but has not yet been shown in humans that the tumoricidal activity of clinically used PARP inhibitors may be related in part to PARP inhibition in the mitochondria. Veliparib (1,2-[(S)-2-methylpyrrolidin-2-yl]-1H-benzimidazole-4-carboxamide, also, ABT-888) is a promising PARP-1 inhibitor that has entered clinical phase I/II trials for several forms of cancer including breast cancer and solid tumor neoplasm, either as a single agent or as a combination with other chemotherapeutics.

It is therefore desirable to develop PARP inhibitors, and especially those with high specific activity and mitochondria-targeting ability.

STATEMENT REGARDING FEDERAL FUNDING

This invention was made with government support under Grant Nos. NS084604 and A1068021 awarded by the National Institutes of Health. The government has certain rights in the invention.

SUMMARY

If suitable PARP inhibitors could be targeted exclusively to the mitochondria, it is feasible that they might prevent potentially lethal $NAD^+$ depletion-associated energy failure and cell death without undesirable effects on genomic DNA repair; and potentially used in tandem with DNA damage-targeting cancer therapies, such as radiation therapy. The present application suggests that mitochondrially-targeted PARP inhibitors may have unique and important advantages over PARP inhibitors that are non-selectively distributed over cellular compartments, including directly preserving $NAD_+$ stores within mitochondria (a primary depot of $NAD_+$ within cells); preventing initiation of MPT pore opening by a mechanism involving PARP-mediated post-translational modification of MPT pore components; and not impacting facilitation of DNA repair by PARP-1 in cell nuclei. Mitochondria-targeting PARP inhibitors could have widespread clinical efficacy in diseases where the pathophysiology includes mitochondrial dysfunction and/or energy failure, and maintaining efficient nuclear DNA repair and genomic integrity is desirable; including but not limited to ischemia reperfusion injury, trauma, sub-lethal radiation injury, neurodegenerative diseases, and overwhelming infection.

Provided herein are mitochondria-targeted PARP inhibitors, such as mitochondria-targeted PARP-1 inhibitors. Based on the data presented below, the disclosed mitochondria-targeted PARP-inhibitors are expected to be therapeutically effective to treat neurodegeneration and other CNS and non-CNS conditions associated with oxidative stress, tissue damage, and cellular energy failure in a patient, as well as in combination with oncolytics. Further, the disclosed mitochondria-targeted PARP-inhibitors are expected to be therapeutically effective to protect a patient against oxidative damage caused by ionizing radiation or tumoricidal agents, for example caused by chemotherapeutics or radiation therapies, a clinical need that has not yet been addressed.

Provided herein according to one aspect is a composition comprising a mitochondria-targeting group covalently linked to a PARP inhibitor, or a pharmaceutically-acceptable salt or ester thereof.

According to a further aspect, a method of reducing $NAD_+$ depletion and cell death induced by oxidative stress in a cell or a patient is provided, comprising administering to a cell or a patient an amount of a compound comprising a mitochondria-targeting group covalently linked to a PARP inhibitor, or pharmaceutically-acceptable salt or ester thereof, effective to decrease $NAD_+$ depletion in mitochondria of a cell or of a patient.

According to a further aspect, a method of reducing cell death induced by mitochondrial dysfunction and/or damage in a cell or a patient, comprising administering to a cell or a patient an amount of a compound comprising a mitochondria-targeting group covalently linked to a PARP inhibitor, or pharmaceutically-acceptable salt or ester thereof, effective to improve mitochondrial function and reduce mitochondrial damage in a cell or in a patient.

According to a further aspect, a method of reducing energy failure induced by ischemia-reperfusion in a cell or a patient, comprising administering to a cell or a patient an amount of a compound comprising a mitochondria-targeting group covalently linked to a PARP inhibitor, or pharmaceutically-acceptable salt or ester thereof, effective to prevent or reduce ischemia-reperfusion injury in a cell or in a patient.

According to a further aspect, a method of reducing cell death caused by exposure to ionizing radiation in a patient, comprising administering to a patient an amount of a compound comprising a mitochondria-targeting group covalently linked to a PARP inhibitor, or pharmaceutically-acceptable salt or ester thereof, effective to decrease mitochondrial and nuclear DNA damage and improve DNA repair in cells of a patient.

Also provided herein according to another aspect is a method of treating a cancer in a patient, comprising administering to a patient an amount of a first compound comprising a mitochondria-targeting group covalently linked to a PARP inhibitor, or pharmaceutically-acceptable salt or ester thereof, effective to sensitize malignant, but not non-malignant, cells of a patient to anti-cancer drugs. Additional chemotherapeutic (anticancer) drugs or treatments can be administered to the patient with the first compound.

BRIEF DESCRIPTION OF THE DRAWINGS

The patent or application file contains at least one drawing executed in color. Copies of this patent or patent application publication with color drawings will be provided by the Office upon request and payment of the necessary fee.

In FIG. 1B: 5-hydroxyisoquinolin-1(2H)-one; 6-amino-1H-benzo[de]isoquinoline-1,3(2H)-dione; 2-nitrophenanthridin-6(5H)-one; PD128763; E7016; and NU1025.

(FIG. 7A) OGD in rat primary cortical neurons treated with 1-100 μM of veliparib or XJB-Veliparib (top panel). Bottom panel showing 1-200 nM concentration range. *P<0.05 vs. naked veliparib; n=6/group. (FIG. 7B) Glutamate-glycine excitotoxicity in primary cortical neurons. Neurons were exposed to 10 μM L-glutamate and 10 μM glycine, with 1-100 μM of XJB-veliparib or nontargeting veliparib for 24 h; *P<0.05 vs. naked veliparib, n=6/group. (FIG. 7C) Glutamate excitotoxicity in an immortalized hippocampal neuronal HT22 cell line. XJB-veliparib and nontargeting veliparib were both effective at inhibiting excitotoxic cell death, with XJB-veliparib slightly more effective at higher doses (*P<0.05 vs. naked veliparib; n=5/group).

DETAILED DESCRIPTION

Figure 1A:
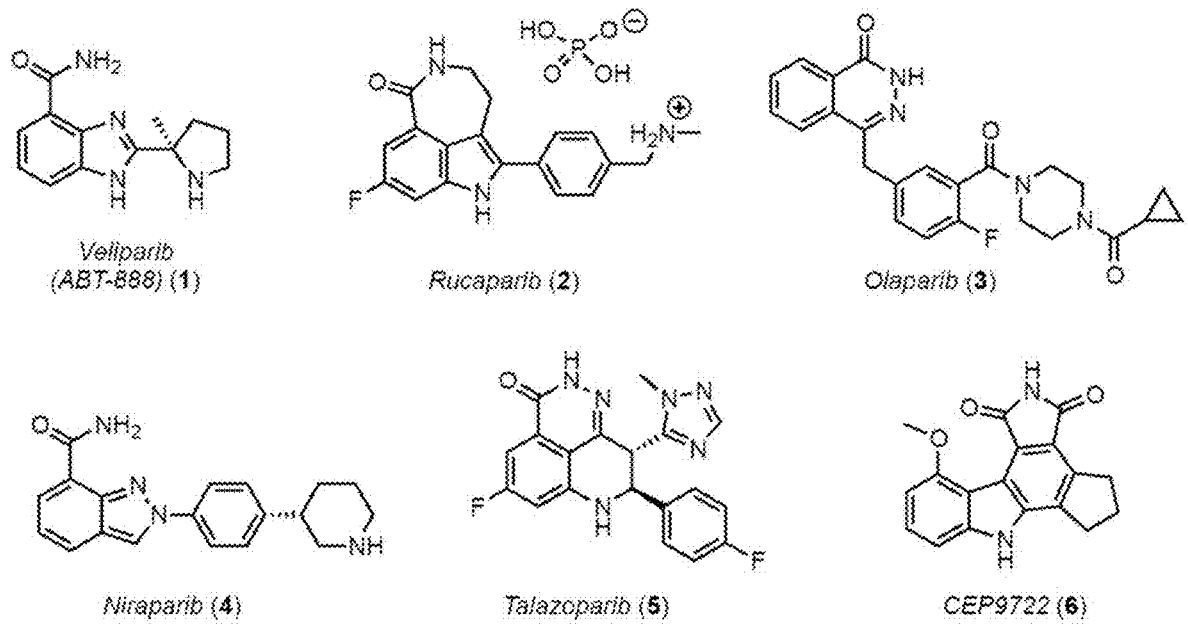
FIG. 1A. PARP inhibitors in clinical use or in current trials.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to human beings.

As used herein, "alkyl" refers to straight, branched chain, or cyclic hydrocarbyl groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—$CH_2$—$CH_2$—). "Optionally substituted alkylene" refers to alkylene or substituted alkylene. "Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Alkyne or "alkynyl" refers to a straight or branched chain unsaturated hydrocarbon having the indicated number of carbon atoms and at least one triple bond.

The term "alkoxy" refers to an —O-alkyl group having the indicated number of carbon atoms. For example, a ($C_1$-$C_6$)alkoxy group includes —O-methyl (methoxy), —O— ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy).

"Aryl," alone or in combination refers to an aromatic monocyclic or bicyclic ring system such as phenyl or naphthyl. "Aryl" also includes aromatic ring systems that are optionally fused with a cycloalkyl ring.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-I-yl, piperazin-1-yl, nitro, sulfato or other R-groups.

Provided herein are mitochondrial-targeted PARP inhibitors and methods of use for those PARP inhibitors. PARP inhibitors that target preferentially to the mitochondria are expected to prevent the potentially lethal side effects of $NAD^+$ depletion-associated energy failure. As described herein, mitochondrially-targeted PARP inhibitors have unique and important advantages over PARP inhibitors that are non-selectively distributed over cellular compartments, including directly preserving $NAD_+$ stores within mitochondria (a primary depot of $NAD_+$ within cells); preventing initiation of MPT pore opening by a mechanism involving PARP-mediated post-translational modification of MPT pore components; and not impacting facilitation of DNA repair by PARP-1 in cell nuclei.

Conditions potentially treatable by the mitochondria-targeting PARP inhibitors described herein include, without limitation ischemia reperfusion injury, trauma including chronic traumatic encephalopathy, sub-lethal radiation injury, neurodegenerative diseases, and overwhelming infection (e.g., sepsis). The data presented below support this. The disclosed mitochondria-targeted PARP-inhibitors are expected to be therapeutically effective to treat neurodegeneration and other CNS and non-CNS conditions associated with oxidative stress, oxidative tissue damage, and cellular energy failure in a patient, and may be superior to non-targeting PARP inhibitors used in combination with oncolytics. Further, the disclosed mitochondria-targeted PARP-inhibitors are expected to be therapeutically effective to protect a patient against oxidative damage caused by ionizing radiation, for example caused by chemotherapeutics or radiation therapies, a clinical need that has not yet been addressed.

Provided herein according to one aspect is a composition comprising a mitochondria-targeting group covalently linked to a PARP inhibitor or a derivative, isostere, or pharmaceutically-acceptable salt or ester thereof.

Also provided herein according to another aspect is a method of treating a cancer in a patient, comprising administering to a patient an amount of a first compound comprising a mitochondria-targeting group covalently linked to a PARP inhibitor, or a pharmaceutically-acceptable salt or ester thereof, effective to treat cancer in a patient, e.g., to sensitize malignant, but not non-malignant (normal) cells in a patient to anti-cancer drugs. Additional chemotherapeutic drugs or treatments may be administered to the patient with the first compound.

According to a further aspect, a method of reducing $NAD_+$ depletion and cell death induced by oxidative stress in a cell or a patient is provided, comprising administering to a cell or a patient an amount of a compound comprising a mitochondria-targeting group covalently linked to a PARP inhibitor, or a pharmaceutically-acceptable salt or ester thereof, effective to decrease NAD$_+$ depletion in mitochondria of a cell or of a patient.

According to a further aspect, a method of reducing cell death induced by mitochondrial dysfunction and/or damage in a cell or a patient, comprising administering to a cell or a patient an amount of a compound comprising a mitochondria-targeting group covalently linked to a PARP inhibitor or a pharmaceutically-acceptable salt or ester thereof effective to improve mitochondrial function and reduce mitochondrial damage in a cell or in a patient.

According to a further aspect, a method of reducing energy failure induced by ischemia-reperfusion in a cell or a patient, comprising administering to a cell or a patient an amount of a compound comprising a mitochondria-targeting group covalently linked to a PARP inhibitor or a pharmaceutically-acceptable salt or ester thereof effective to prevent or reduce ischemia-reperfusion injury in a cell or in a patient.

According to a further aspect, a method of reducing irradiation (IR)-induced cell death and mitochondrial DNA (mtDNA) damage from exposure to ionizing radiation in a patient, comprising administering to a patient an amount of a compound comprising a mitochondria-targeting group covalently linked to a PARP inhibitor, or a pharmaceutically-acceptable salt or ester thereof, effective to reduce irradiation (IR)-induced cell death and mitochondrial DNA (mtDNA) damage in a patient.

A "mitochondrial targeting moiety" is a moiety (that is, a part of a molecule) that partitions specifically to mitochondria, including their inner compartments and/or membranes. In one aspect, the mitochondria targeting group is a peptide fragment derived from gramicidin, such as a mitochondria-targeting gramicidin peptide isostere, examples of which follow, e.g., Leu-$^D$Phe-Pro-Val-Orn and $^D$Phe-Pro-Val-Orn-Leu hemigramicidin fragments and isosteres thereof. Because gramicidin is cyclic, any hemigramicidin 5-mer is expected to be useful as a membrane active peptide fragment, including Leu-$^D$Phe-Pro-Val-Orn, $^D$Phe-Pro-Val-Orn-Leu, Pro-Val-Orn-Leu-$^D$Phe, Val-Orn-Leu-$^D$Phe-Pro, and Orn-Leu-$^D$Phe-Pro-Val (from gramicidin S). Any larger or smaller fragment of gramicidin, or even larger fragments containing repeated gramicidin sequences (e.g., Leu-$^D$Phe-Pro-Val-Orn-Leu-$^D$Phe-Pro-Val-Orn-Leu-$^D$Phe-Pro) are expected to be useful for membrane targeting, and can readily be tested for such activity. In one aspect, the gramicidin S-derived peptide comprises a β-turn, which appears to confer to the peptide a high affinity for mitochondria. Derivatives of gramicidin, or other antibiotic fragments, include isosteres, such as (E)-alkene isosteres (see, United States Patent Publication Nos. 2007/0161573 and 2007/0161544, incorporated herein by reference in their entirety, for exemplary synthesis methods).

In one aspect, an alkene peptide isostere segment of the antibiotic gramicidin S (GS), the XJB mitochondria-targeting moiety described herein, acts as an effective mitochondrial targeting vector. The presence of a type II' β-turn in this pentapeptide sequence facilitates membrane permeability since the polar functionality of the backbone is less solvent-exposed and intramolecular hydrogen bonding is favored.

Figure 2:
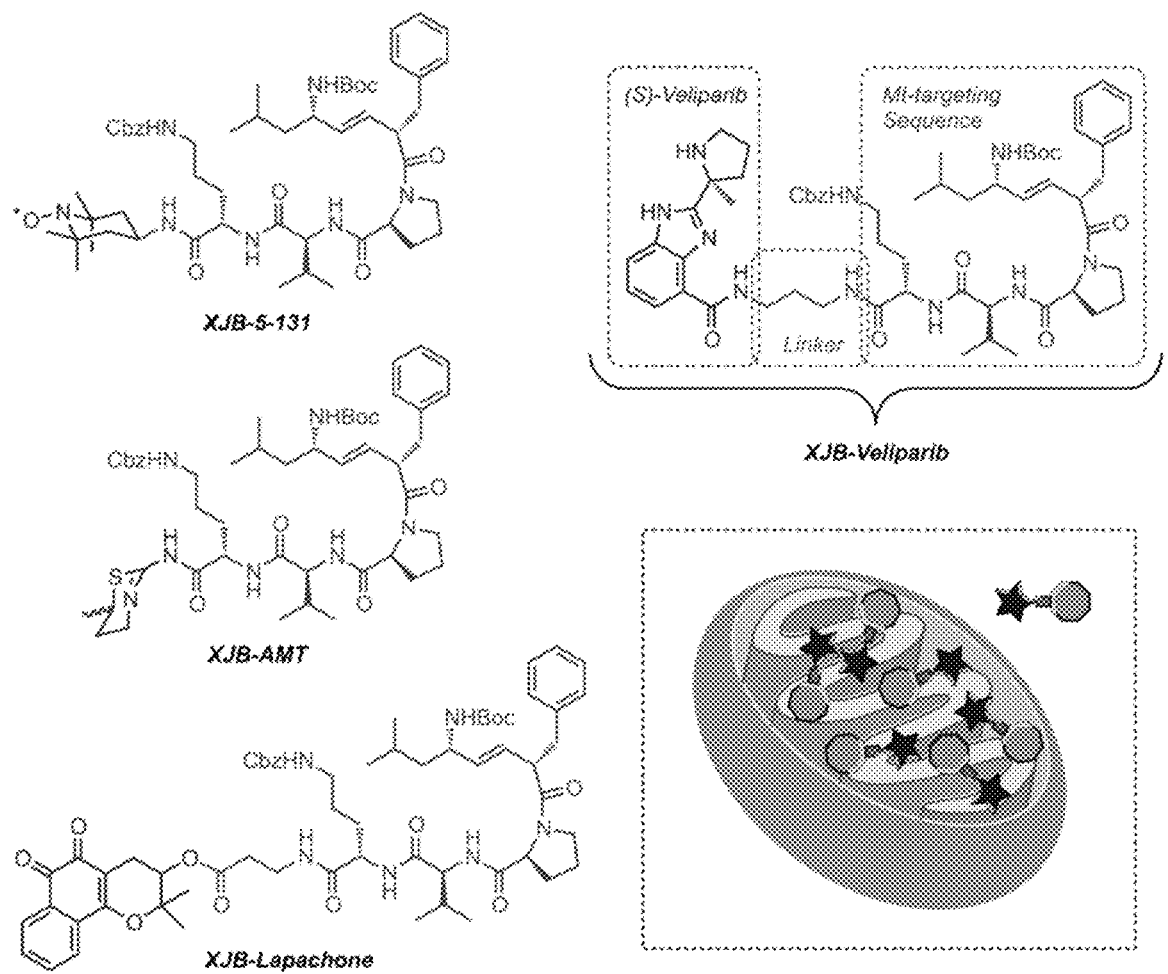
FIG. 2. Mitochondrially targeted 4-amino-TEMPO (XJB-5-131), lapachone (XJB-lapachone) and veliparib (XJB-veliparib). The therapeutically active payload, the linker region, and the XJB mitochondrial targeting moiety are shown in the mitochondria diagram.

In one aspect, for example as illustrated by the Examples below, the XJB hemigramicidin S pentapeptide isostere is selected as the targeting unit (FIG. 2). The alkene peptide isostere segment in XJB is a surrogate of the leucyl-d-phenylalanine dipeptide in the bacterial membrane-associated antibiotic gramicidin S (GS), and its side chain-protected ornithylvalylproline tripeptide subunit is taken directly from GS. The D-Phe-Pro sequence is based on the reverse turn inducing sequence of GS that activates a type II' β-turn structure that buries several polar amide groups inside the molecule and thus may facilitate membrane transport. This moiety has previously been used in combination with a nitroxide payload to generate XJB-5-131, a reactive oxygen scavenger that validated the targeting design and was found to be ca. 600-fold enriched in mitochondria over the cytosol. XJB-5-131 has shown in vivo efficacy in rodent models of Huntington's disease (HD), traumatic brain injury (TBI), ischemia-reperfusion injury, and hemorrhagic shock. In the radiation protector XJB-AMT, a nitric oxide synthase (NOS) antagonist (AMT) is conjugated to the targeting sequence, with the goal to counteract the activation of mitochondrial NOS by ionizing radiation, which can lead to inhibition of the respiratory chain, a burst of superoxide and peroxynitrite, and cellular damage. XJB-Lapachone introduces a derivative of the natural product β-lapachone into mitochondria and causes extensive cellular vacuolization and autophagy, as well as stimulating ROS generation in mitochondria.

In one aspect, the compound has the structure:

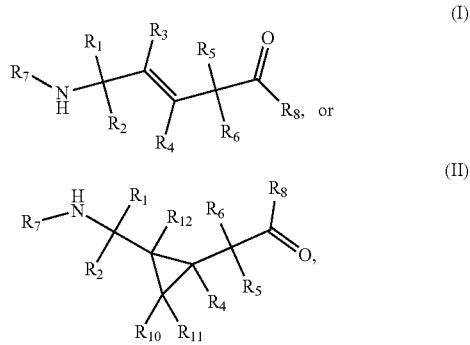

wherein $R_1$, $R_2$, $R_5$, and $R_6$ are independently hydrogen, hydroxyl, halo, a $C_1$-$C_6$ straight or branched-chain alkyl, or a $C_1$-$C_6$ straight or branched-chain alkyl further comprising a phenyl group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted, for example, and without limitation, $R_1$, $R_2$, $R_5$, and $R_6$ are independently methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl, or hydroxyphenyl;

$R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_7$ is —C(O)—$R_{13}$, —C(O)O—$R_{13}$, or —P(O)—($R_{13}$)$_2$, wherein $R_{13}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_7$ is Ac (Acetyl, R=—C(O)—CH$_3$), Boc (R=—C(O)O-tert-butyl), Cbz (R=—C(O)O-benzyl (Bn)), or a diphenylphosphate group;

$R_8$ is —NH—$R_9$, —O—$R_9$, —CH$_2$—$R_9$, -L-$R_9$, —NH-L-$R_9$, or —O-L-$R_9$, where $R_9$ is a PARP inhibitor or a derivative thereof, such as such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g., CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, and where L is a $C_{1-5}$ alkyl linker, optionally comprising an ester or amide linkage;

$R_3$ is a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; and $R_{10}$, $R_{11}$, and $R_{12}$ are independently H or halogens (See, e.g., International Patent Publication Nos. WO 2010/009405 and WO 2012/112851, incorporated herein by reference in their entirety).

In another aspect, the compound has the structure:

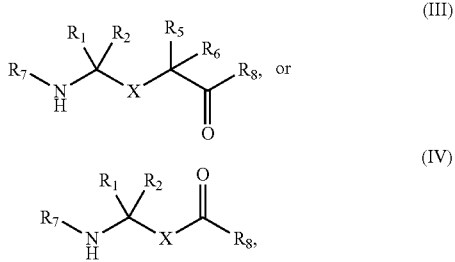

(III)

(IV)

wherein X is

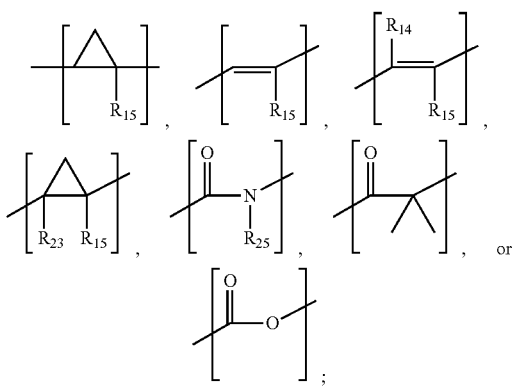

$R_1$, $R_2$, $R_5$, $R_6$, and $R_{14}$ are each independently hydrogen, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_8$ is —NH—$R_9$, —O—$R_9$, —CH$_2$—$R_9$, -L-$R_9$, —NH-L-$R_9$, or —O-L-$R_9$, where $R_9$ is a PARP inhibitor or a derivative thereof, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, and where L is a $C_{1-5}$ alkyl linker, optionally comprising an ester or amide linkage; and $R_7$ is —C(O)—$R_{13}$, —C(O)O—$R_{13}$, or —P(O)—($R_{13}$)$_2$, wherein $R_{13}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_7$ is Ac (Acetyl, R=—C(O)—CH$_3$), Boc (R=—C(O)O-tert-butyl), Cbz (R=—C(O)O-benzyl (Bn)), or a diphenylphosphate group.

Non-limiting examples of compounds according to (V) include:

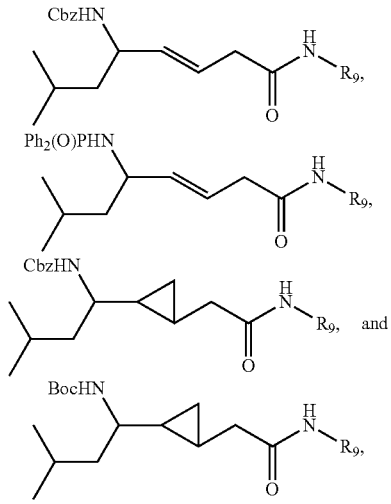

wherein $R_9$ is a PARP inhibitor or a derivative thereof, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof.

In one aspect, the compound has a structure chosen from:

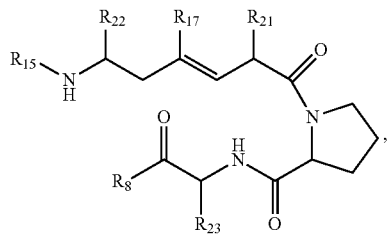

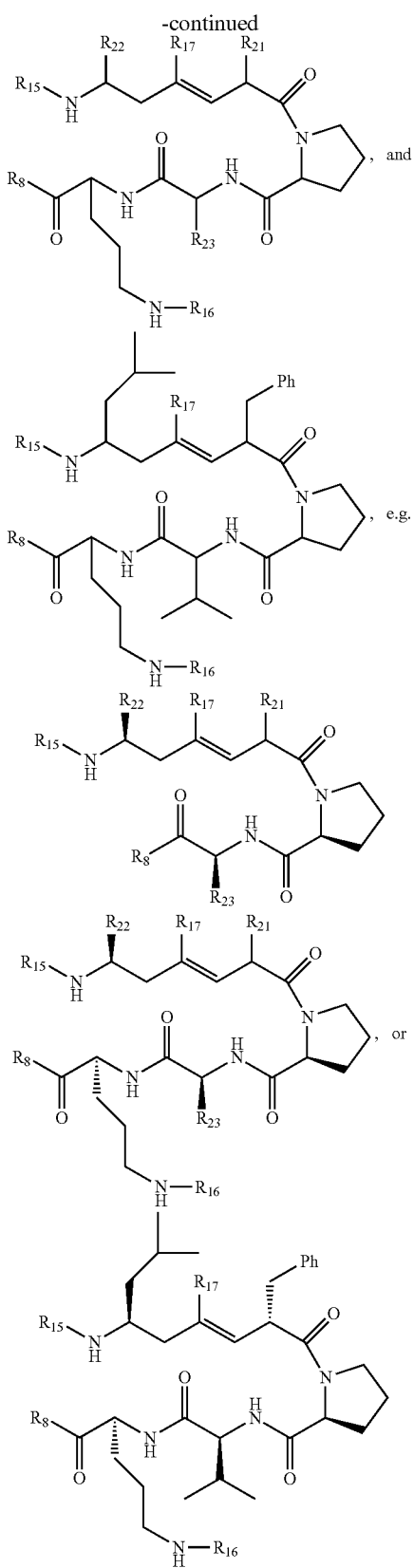

wherein $R_8$ is —NH—$R_9$, —O—$R_9$, —CH$_2$—$R_9$, -L-$R_9$, —NH-L-$R_9$, or —O-L-$R_9$, where $R_9$ is a PARP inhibitor, such as, olaparib, veliparib, CEP-8983 (II-methoxy-4,5,6,7-tetrahydro-IH-cyclopenta[a]pyrrolo[3,4-c]carbazole-I,3 (2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, and where L is a $C_{1-5}$ alkyl linker, optionally comprising an ester or amide linkage; $R_{15}$ and $R_{16}$, independently are an amine protecting group or acylated (the N is acylated). $R_{21}$ is H or $C_{1-3}$ alkyl aryl, such as methylphenyl (—CH$_2$-Ph). $R_{22}$ and $R_{23}$ are, independently, H, $C_{1-4}$alkyl or hetero-substituted alkyl, such as a thioether, for example and without limitation, an aliphatic amino acid side chain, such as

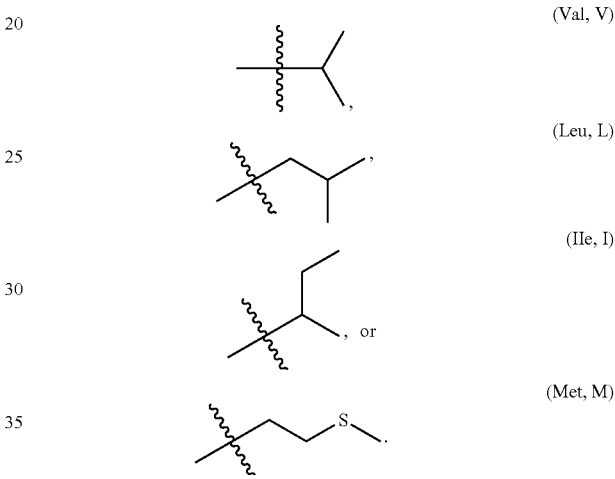

In aspects, In one aspect, $R_{15}$ and $R_{16}$ are protecting groups independently selected from the group consisting of: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT), and $R_{17}$ is H or methyl. In one aspect, $R_{15}$ is Boc and $R_{16}$ is Cbz. Ph is phenyl.

In another aspect, the compound has the structure:

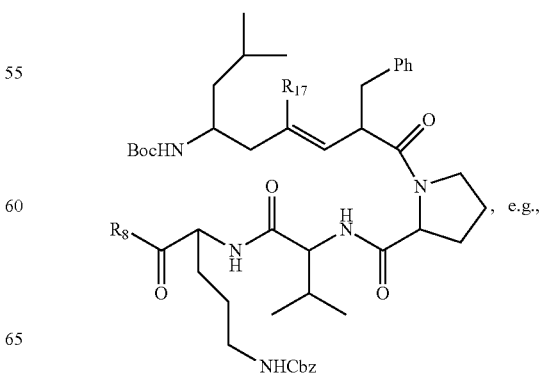

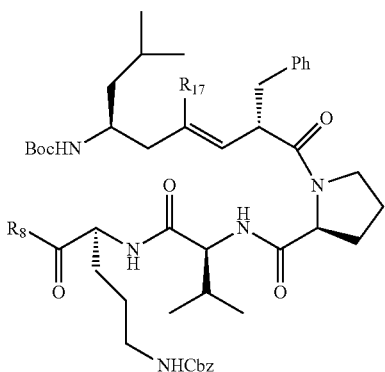

wherein $R_8$ is —NH—$R_9$, —O—$R_9$, —CH$_2$—$R_9$, -L-$R_9$, —NH-L-$R_9$, or —O-L-$R_9$, where $R_9$ is a PARP inhibitor or a derivative thereof, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, $R_{17}$ is H or methyl, and where L is a C$_{1-5}$ alkyl linker, optionally comprising an ester or amide linkage. In one aspect, in any of the compounds described herein, $R_8$ is:

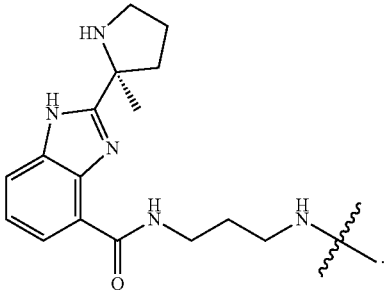 [SMILES: *NCCCNC(=O)c1cccc2[nH]c([C@]3(C)CCCN3)nc12]

In another aspect, the compound has the structure:

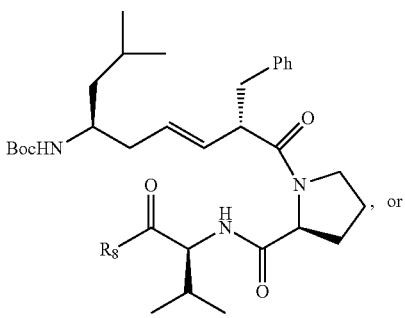

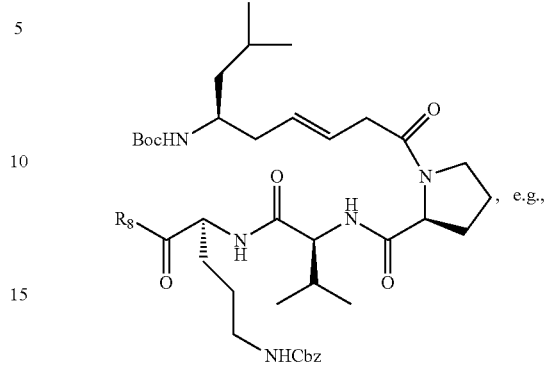

, e.g.,

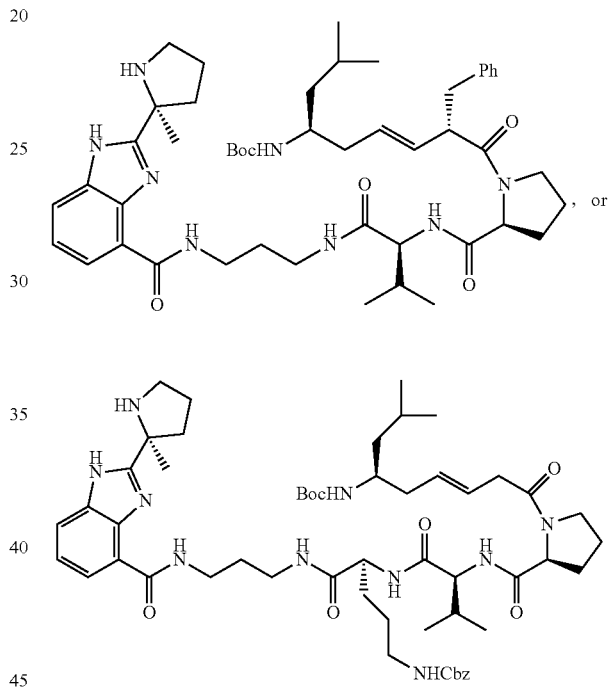

, or

In another aspect, the compound has the structure:

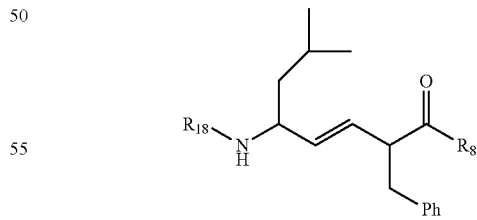

wherein $R_8$ is —NH—$R_9$, —O—$R_9$, —CH$_2$—$R_9$, -L-$R_9$, —NH-L-$R_9$, or —O-L-$R_9$, where $R_{20}$ is a PARP inhibitor or a derivative thereof, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, and where L is a $C_{1-5}$ alkyl linker, optionally comprising an ester or amide linkage, and $R_{18}$ is an amine protecting group or acylated (the N is acylated).

As used herein, unless indicated otherwise, for instance in a structure, all compounds and/or structures described herein comprise all possible stereoisomers, individually or mixtures thereof, including any pharmaceutically-acceptable salts thereof.

Figure 1B:
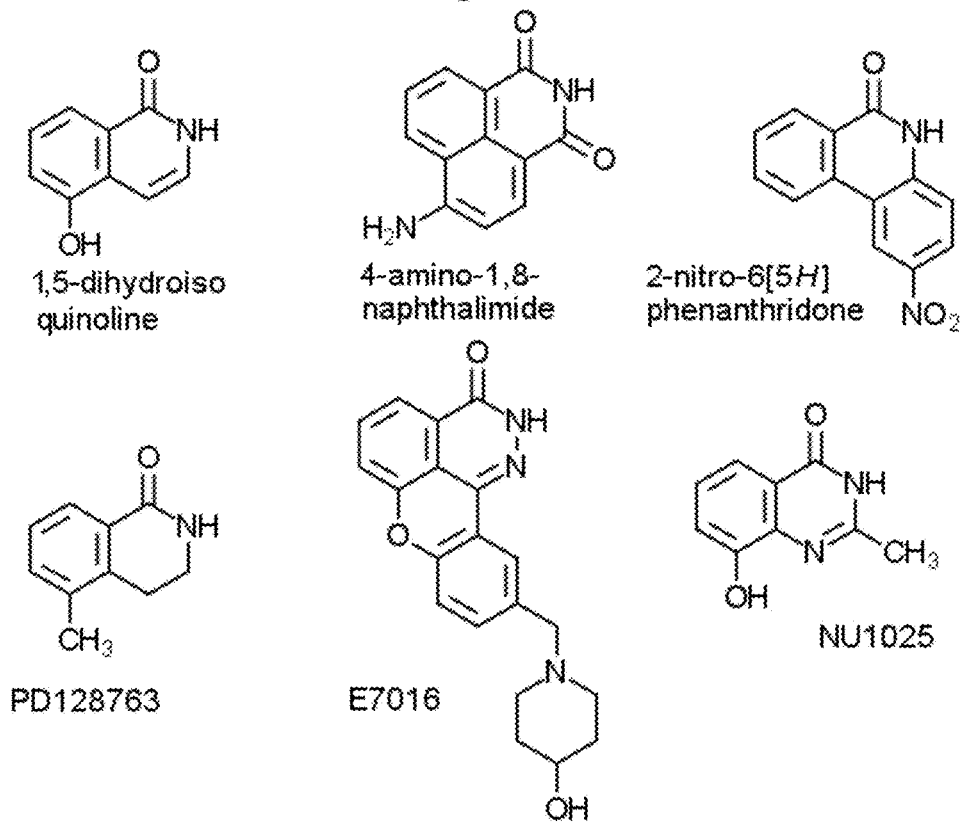
FIG. 1B.

A "PARP inhibitor" is an inhibitor of PARP-1, PARP-2, or PARP-3, though at this time, they are predominantly PARP-1 inhibitors. Non-limiting example of PARP inhibitors, that also can be classified as PARP-1 inhibitors, include olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof (See, e.g., FIGS. 1A and 1B and Curtin N.J., et al. Therapeutic applications of PARP inhibitors: anticancer therapy and beyond. *Molecular aspects of medicine* 2013; 34:1217-56). As an example, veliparib has the structure:

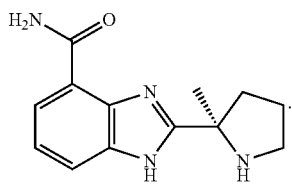 [SMILES: C[C@]1(c2nc3c(C(N)=O)cccc3[nH]2)CCCN1]

Attachment (covalent linking) of the PARP inhibitor to the mitochondria-targeting group (see, e.g., FIG. 2) can be achieved by any useful chemistry, so long as the composition substantially retains its pharmacological effect. For example, as in the examples below, veliparib is linked to a mitochondria-targeting group through its amide (carboxamide) group as in the following structure:

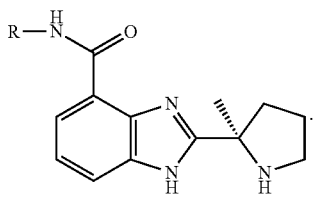

where R is a mitochondria-targeting moiety according to any aspect described herein, and optionally comprises a linker between the mitochondria-targeting group and the veliparib moiety, e.g.,

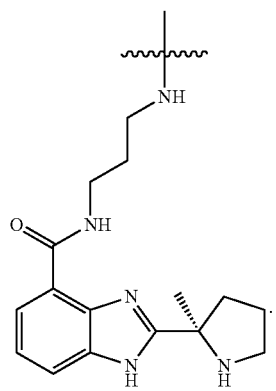 [SMILES: *NCCCNC(=O)c1cccc2[nH]c([C@@]3(C)CCCN3)nc12]

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned herein are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely the salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and valyl.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

As used herein, unless indicated otherwise, for instance in a structure, all compounds and/or structures described herein comprise all possible stereoisomers, individually or mixtures thereof. The compound and/or structure may be an enantiopure preparation consisting essentially of an (−) or (+) enantiomer of the compound, or may be a mixture of enantiomers in either equal (racemic) or unequal proportions.

As used herein, a ring structure showing a bond/group that is not attached to any single carbon atom, for example and without limitation, depicted as

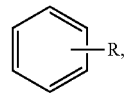

can be substituted at any position with one or more groups designated "R", and, unless indicated otherwise, each instance of R on the ring can be (independently) the same or different from other R moieties on the ring. Thus, if R is H, the group contains nothing but H groups. If R is "halo", it is a single halo (e.g., F, Cl, Br and I) group. If R is one or more independently of halo and CN, the ring may comprise one, two, three, four, halo or CN groups, such as, for example and without limitation: 2, 3, 4, or 5 chloro; 2, 3, 4, or 5 bromo; 2,3- or 3,4- or 4,5- or 2,4-dichloro; 3-bromo-4-chloro; 3-bromo-4-cyano, and any other possible permutation of the listed groups.

Protected derivatives of the disclosed compounds also are contemplated. Many suitable protecting groups for use with the disclosed compounds are broadly-known in the art. In general, protecting groups are removed under conditions which will not affect the remaining portion of the molecule. These methods are well known in the art and include acid hydrolysis, hydrogenolysis and the like. One method involves the removal of an ester, such as cleavage of a phosphonate ester using Lewis acidic conditions, such as in TMS-Br mediated ester cleavage to yield the free phosphonate. A second method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with any of the large number of broadly-available publications. When an amine is deprotected, the resulting salt can readily be neutralized to yield the free amine. Similarly, when an acid moiety, such as a phosphonic acid moiety is unveiled, the compound may be isolated as the acid compound or as a salt thereof.

According to one aspect, amine side chains are protected using protective groups, for example and without limitation by acylation (See, e.g., U.S. Pat. Nos. 7,528,174; 7,718,603; and 9,006,186, and International Patent Publication Nos. WO 2010/009405 and WO 2012/112851, incorporated herein by reference in their entirety). Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) groups. A protecting group also includes acyl groups, such as acetyl groups, for example, as described.

A linker is a group that covalently attaches, in the context of the compositions described herein, the mitochondrial-targeting moiety and the PARP inhibitor moiety. The linker does not interfere with the pharmacological effects of the composition as a whole. Examples of linkers include aliphatic hydrocarbons, or aliphatic hydrocarbons having one or more aromatic groups in their structure, such as saturated or unsaturated $C_{1-10}$ hydrocarbon moieties, e.g., a linear or branched saturated $C_1$-$C_{10}$ alkyl. A linker, prior to incorporation into a compound comprises active groups, e.g., carboxyl, alkoxyl, amino, sulfhydryl, amide, etc., and a non-reactive moiety that remains once the linker is incorporated into a compound. The non-reactive moiety (such as saturated alkyl or phenyl) does not interfere, sterically or by any other physical or chemical attribute, such as polarity or hydrophobicity/hydrophilicity, in a negative (loss of function) capacity with respect to the pharmacological activity of the overall compound. Linker and linking chemistry is broadly-known, and in one example, is carbodiimide chemistry using EDC (1-Ethyl-3-(3-dimethylaminopropyl)carbodiimide) or DCC (N',N'-dicyclohexyl carbodiimide) chemistry as used in the Examples below (see, FIG. 3) to couple amines and carboxyl groups. Listing all linking chemistries are broadly-known and thus are beyond the scope of this disclosure (see, e.g. *Thermo Scientific Crosslinking Technical Handbook*, Thermo Fisher Scientific, Inc. 2012.).

The compounds typically are administered in an amount and dosage regimen to treat (a) a cancer (e.g., a malignancy), which includes, without limitation, any abnormal cells that divide without control and can invade nearby tissues, or (b) a hyperplasia, which is an increase in the number of cells in an organ or tissue, where the cells appear normal, and are not a cancer, but may become cancer. The compounds also are useful in mitigating radiation damage. For example, at concentrations of 5 µM or more XJB-veliparib decreased radiation damage, as described in the examples below. The compounds also are expected to be useful in treatment of neurodegeneration includes treatment of neurodegenerative diseases, such as Parkinson's disease (PD), Alzheimer's disease (AD), Multiple Sclerosis (MS) chronic traumatic encephalopathy (CTE), and amyotrophic lateral sclerosis (ALS). The compounds may be administered in any manner that is effective to treat, mitigate or prevent any of the above conditions, including cancer, hyperplasia, neurodegeneration, PD, AD, MS, CTE, and ALS. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

As indicated above, and in the examples, the compounds exhibit PARP-inhibiting, e.g. PARP-1-inhibiting, activities, at dosages of >0 µM, e.g., >1 nM, with the upper limit being dictated by toxicity, for example direct cellular exposure of up to 10 µM of the compound, e.g., as described in the examples below. Therefore, an "effective amount" of the compound or composition described herein is an amount effective in a dosage regimen (amount of the compound and timing of delivery), to achieve a desired end-point, such as maintaining concentrations at a site of treatment within a range effective to achieve an outcome. Suitable outcomes include killing of cancer cells, improvement or maintenance of neurological function, cellular protection including neuroprotection, shrinking a tumor, reducing $NAD^+$ depletion, or mitigating radiation damage to ionizing radiation.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one aspect, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a non-woven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. Certain formulations that may be useful as permeation enhancers include, without limitation: DMSO; 95% Propylene Glycol+5% Linoleic Acid; and 50% EtOH+40% HSO+5% Propylene Glycol+5% Brij30.

Therapeutic/pharmaceutical compositions are prepared in accordance with acceptable pharmaceutical procedures.

In one aspect, the compositions as described a combined with other drugs or therapies, such as anticancer therapies, such as chemotherapeutic or radiation therapies, as are known in the art. Therefore in one aspect, a method of treatment of a cancer is provided, comprising treating the cancer with a composition comprising a compound comprising a mitochondria-targeting moiety covalently linked to a PARP inhibitor or a derivative thereof, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4 (3H)-one), 1,5-dihydroiso quinoline, 4-amino-1,8-naphthalimide, 2-nitro-6[5H]phenanthridinone, PD128763, and analogues, isosteres, and derivatives thereof according to any aspect described herein and either co-administering a second chemotherapeutic agent, or applying a radiation therapy to the patient while the compound is present in the patient.

Chemotherapeutic agents are compounds or compositions used to treat cancer, including, for example and without limitation: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvincaleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyureataxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, and vinflunine, and pharmaceutically acceptable salts thereof.

Example 1

Figure 3:
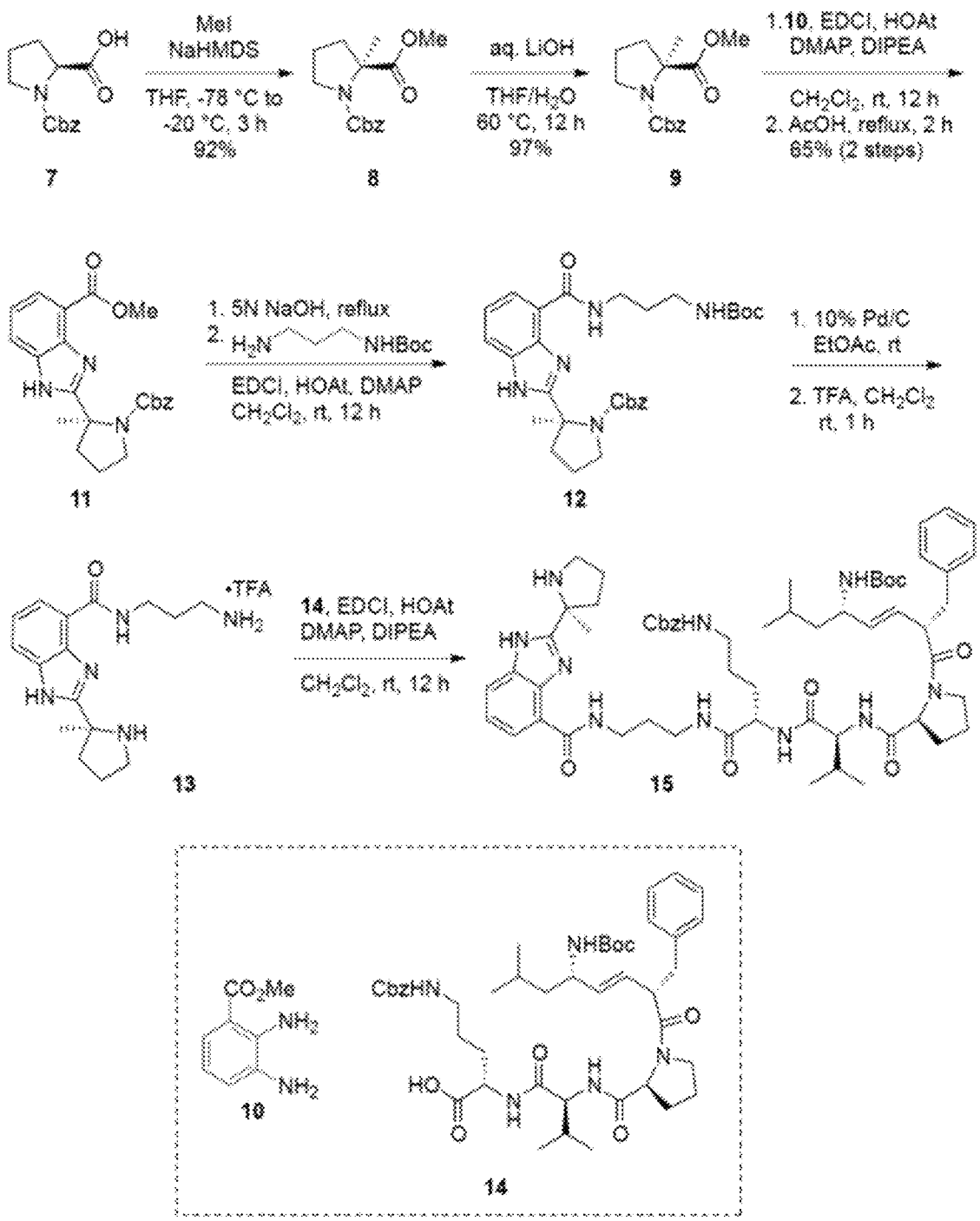
FIG. 3. Synthesis of XJB-Veliparib (15).

Synthesis of XJB-veliparib: The chemical synthesis of the mitochondria-targeting XJB-veliparib hybrid molecule is shown in FIG. 3. The XJB pentapeptide isostere was chosen as the targeting unit (FIG. 2). For the synthesis of mitochondrially targeted veliparib, XJB-Veliparib, N-Cbc-L-proline methyl ester (7) was treated with NaHMDS and MeI followed by hydrolysis to give the acid 9 in 98% yield over 2 steps (Scheme 1). One-pot EDCl coupling to methyl 2,3-diaminobenzoate (10) and acid-catalyzed cyclization provided the benzimidazole 11 in good overall yield. Hydrolysis of the methyl ester followed by acylation with the N-Boc-1,3-diaminopropane spacer group afforded 12. Removal of the Cbz-group via hydrogenation followed by Boc-deprotection provided 13, which was coupled to the Boc-Leu-D-Phe-Pro-Val-Orn(Cbz)-OH targeting sequence 14 to afford the desired XJB-Veliparib conjugate 15.

In further detail, all moisture- and air-sensitive reactions were performed in oven dried glassware under a positive pressure of argon. All reagents and solvents were used as received unless otherwise specified. THE and $Et_2O$ were distilled over sodium/benzophenone ketyl; $CH_2Cl_2$ was distilled over $CaH_2$, MeCN and DMF were dried over molecular sieves. Reactions were monitored by TLC analysis (pre-coated silica gel 60 $F_{254}$ plates, 250 µm layer thickness) and visualization was accomplished with a 254/280 nm UV light and/or by staining with $KMnO_4$ solution (1.5 g $KMnO_4$ and 1.5 g $K_2CO_3$ in 100 mL of a 0.1% NaOH solution), a ninhydrin solution (2 g ninhydrin in 100 mL EtOH), a PMA solution (5 g phosphomolybdic acid in 100 mL EtOH), or a p-anisaldehyde solution (2.5 mL p-anisaldehyde, 2 mL AcOH and 3.5 mL conc. $H_2SO_4$ in 100 mL EtOH). Flash chromatography was performed on silica gel (40-63 µm). Melting points were determined on a Mel-Temp II capillary melting point apparatus fitted with a Fluke 51 II digital thermometer. Infrared spectra were recorded on an ATR spectrometer. NMR spectra were recorded on 300, 400, 500 or 700 MHz instruments. Chemical shifts were reported in parts per million (ppm) and referenced to residual solvent. $^1H$ NMR spectra are tabulated as follows: chemical shift, multiplicity (br=broad, s=singlet, d=doublet, t=triplet, q=quartet, m=multiplet), coupling constant(s), number of protons. $^{13}C$ NMR spectra were obtained using a proton-decoupled pulse sequence and are tabulated by observed peak. LC-MS analyses were performed on a Shimadzu UFLC instrument equipped with an Applied Biosystem MDS SCIEX API 2000 mass spectrometer (ESI), under the following conditions: column: Varian Polaris C18-A (100× 4.6 mm, 5 µm) equilibrated at 40° C.; buffer A: 0.1% aqueous AcOH, buffer B: 0.1% AcOH in MeCN; 30 min gradient: 5% buffer B in buffer A for 1 min, then 5 to 95% buffer B in buffer A over 13 min, then 95% buffer B in buffer A for 4 min, then 95-5% buffer B in buffer A over 7 min, then 5% buffer B in buffer A for 5 min; flow rate: 0.2 mL/min; detection: TIC and/or UV A=254/280 nm.

1-benzyl 2-methyl (S)-2-methylpyrrolidine-1,2-dicarboxylate (8). To a −78° C. solution of N—Z-L-proline methyl ester 7 (0.43 mL, 1.9 mmol) and iodomethane (0.24 mL, 3.8 mmol) in THE (3.5 mL) was added NaHMDS (1 M in THF, 3.8 mL, 3.8 mmol) dropwise. The resulting mixture was warmed to −20° C. and stirred at this temperature for 3 h. The mixture was quenched with $H_2O$, acidified with 2N HCl and extracted with EtOAc (3×). The combined organic layers were washed with brine (1×), dried over $MgSO_4$, filtered and concentrated to dryness. The residue was purified by chromatography on $SiO_2$ (30% EtOAc/hexanes) to give 8 as a pale yellow oil (0.52 g, 99%). Spectral data are in accordance with literature values (Penning, T. D., et al., Discovery of the Poly(ADP-ribose) Polymerase (PARP) Inhibitor 2-[(R)-2-methylpyrrolidin-2-yl]-1H-benzimidazole-4-carboxamide (ABT-888) for the Treatment of Cancer. *J. Med. Chem.* 2009, 52, 514-523). $^1H$ NMR (300 MHz, $CDCl_3$) δ 1.54 (s, 1.5H), 1.61 (s, 1.5H), 1.86-1.99 (m, 3H), 2.13-2.24 (m, 1H), 3.46 (s, 1.5H), 3.56-3.69 (m, 2H), 3.71 (s, 1.5H), 4.99-5.23 (m, 2H), 7.24-7.40 (m, 5H) (as a mixture of two rotamers).

(S)-1-((benzyloxy)carbonyl)-2-methylpyrrolidine-2-carboxylic acid (9). Methyl ester 8 (1.53 g, 5.52 mmol) was dissolved in THE (10.5 mL) and $H_2O$ (5.4 mL) and treated with a solution of LiOH (265 mg, 11.0 mmol) in $H_2O$ (5.4 mL). MeCOH (1.5 mL) was then added and the resulting homogenous solution heated to 60° C. overnight. The organic solvents were removed and the aq. layer acidified to pH 2 using 2N HCl and extracted with EtOAc (3×). The combined organic layers were washed with water (1×), dried ($MgSO_4$) filtered and concentrated to dryness to give 9 as a white solid (1.42 g, 98%): Spectral data are in accordance with literature values (Penning, T. D., et al., *J. Med. Chem.* 2009, 52, 514-523). $^1$H NMR (500 MHz, DMSO-d$_6$) δ 1.44 (s, 1.5H), 1.45 (s, 1.5H), 1.80-1.96 (m, 3H), 2.02-2.19 (m, 1H), 3.43-3.53 (m, 2H), 4.94-5.11 (m, 2H), 7.24-7.41 (m, 5H), 12.51 (br s, 1H) (as a mixture of two rotamers).

Methyl (S)-2-(1-((benzyloxy)carbonyl)-2-methylpyrrolidin-2-yl)-1H-benzo-[d]imidazole-4-carboxylate (11). To a solution of 9 (200 mg, 0.760 mmol) and Methyldiaminobenzoate 10 (189 mg, 1.14 mmol) in CH$_2$Cl$_2$ (15 mL) was added DIPEA (0.13 mL, 0.76 mmol) followed by addition of EDCI (218 mg, 1.14 mmol), HOAt (155 mg, 1.14 mmol) and DMAP (9.3 mg, 0.076 mmol) and the resulting solution was stirred at rt overnight. The reaction mixture was quenched with sat. aq. NH4Cl solution and extracted with portions of CH$_2$Cl$_2$ (2×). The combined organic layers were washed with brine (1×), dried (MgSO$_4$), filtered and evaporated to give the coupled product as a brown oil. The crude residue was redissolved in AcOH (5 mL) and heated at reflux for 2 h. The solvent was evaporated, the crude poured onto sat. aq. NaHCO$_3$ and extracted with EtOAc (3×). The combined organic layers were washed with brine (1×), dried (MgSO$_4$) and the solvent evaporated. The crude residue was purified via chromatography on SiO$_2$ (30-90% EtOAc/hexanes) to give 11 as a pale yellow oil (198 mg, 65% over 2 steps): HRMS (ESI$^+$) m/z calcd for C$_{22}$H$_{24}$N$_3$O$_4$ [M+H] 394.1761, found 394.1758.

(S)-2-(1-((benzyloxy)carbonyl)-2-methylpyrrolidin-2-yl)-1H-benzo[d]imidazole-4-carboxylic acid. Methyl ester 11 (280 mg, 0.712 mmol) was dissolved in THF/H$_2$O (14:1, 21 mL) and cooled to −5° C. A 40% n-Bu$_4$NOH (aq.) solution (4.6 mL, 7.1 mmol) was added slowly and the reaction mixture stirred for 30 min at −5° C. and at rt over night. The solution was acidified with aq. AcOH and extracted with portions of EtOAc (3×). The combined organic layers were washed with brine, dried (MgSO$_4$), filtered and the solvent removed under reduced pressure. The crude was purified via column chromatography on SiO$_2$ (0-10% MeOH/CH$_2$Cl$_2$) to give (S)-2-(1-((benzyloxy)carbonyl)-2-methylpyrrolidin-2-yl)-1H-benzo[d]imidazole-4-carboxylic acid as a pale-yellow foam (215 mg, 80%): $^1$H NMR (400 MHz, DMSO-d$_6$) δ 7.86 (br s, 1H), 7.78 (d, J=7.5 Hz, 1H), 7.41-7.36 (m, 4H), 7.33-7.30 (m, 1H), 7.30-7.25 (m, 1H), 7.06 (t, J=7.4 Hz, 0.5H), 6.91 (t, J=7.0 Hz, 1H), 6.70 (br s, 1H), 5.15-5.09 (m, 0.5H), 5.07-5.04 (m, 1H), 3.87-3.54 (m, 3H), 2.76 (br s, 1H), 1.92 (s, 3H), 1.87 (br s, 2H), 1.86 (br s, 1H); $^{13}$C-NMR (700 MHz, DMSO-d$_6$) δ 167.5, 160.5, 159.8, 154.4, 154.1, 137.4, 136.8, 128.9, 128.2, 127.9, 127.7, 127.1, 124.4, 124.3, 121.7, 66.3, 66.2, 62.9, 55.4, 48.8, 48.3, 42.7, 40.5, 24.4, 24.2, 22.9, 22.4; IR (ATR, neat) 1682.8, 1407.6, 1351.5, 1255.8, 746.4 cm$^{-1}$; Mp 102.3-104.6° C.; HRMS (ESI$^+$) m/z calcd for C$_{21}$H$_{22}$N$_3$O$_4$ [M+H] 380.1605, found 380.1610.

benzyl (S)-2-(4-((3-((tert-butoxycarbonyl)amino)propyl) carbamoyl)-1H-benzo-[d]imidazol-2-yl)-2-methylpyrrolidine-1-carboxylate (12). To a solution of N-Boc-1,3-propanediamine (0.28 mL, 1.6 mmol) and 11a (342 mg, 1.05 mmol) in CH$_2$Cl$_2$ (12 mL) at 0° C. was added DIPEA (0.46 mL, 2.6 mmol) followed by the dropwise addition of T$_3$P (50 wt % in EtOAc, 0.92 mL, 1.6 mmol). The resulting mixture was warmed and stirred at rt overnight, washed with 5% aq. Na$_2$CO$_3$ and brine, dried (MgSO$_4$), filtered and evaporated. The crude was purified via chromatography on SiO$_2$ (100% CH$_2$Cl$_2$ to 10% MeOH/CH$_2$Cl$_2$) to give 12 as a pale-yellow foam (503 mg, 89%): $^1$H NMR (600 MHz, DMSO-d$_6$) δ 12.76 (br s, 0.5H), 12.69 (br s, 0.5H), 9.93 (br s, 1H) 7.86-7.80 (m, 1H), 7.64 (d, J=7.7 Hz, 0.5H), 7.60 (d, J=7.7 Hz, 0.5H), 7.39-7.34 (m, 2H), 7.33-7.27 (m, 2H), 6.94-6.81 (m, 2H), 6.73-6.65 (m, 1H), 5.09-4.97 (m, 1H), 4.94-4.79 (m, 1H), 3.86-3.77 (m, 1H), 3.70-3.60 (m, 1H), 3.47-3.37 (m, 2H), 3.11-3.00 (m, 2H), 2.28-2.10 (m, 2H), 2.02-1.94 (m, 2H), 1.91 (br s, 1.5H), 1.89 (br s, 1.5H), 1.73-1.65 (m, 3H), 1.38 (s, 9H); $^{13}$C-NMR (600 MHz, DMSO-d$_6$) δ 165.1, 160.4, 160.2, 156.1, 154.1, 153.7, 140.7, 140.6, 137.5, 136.7, 135.3, 135.2, 128.8, 128.2, 127.8, 127.7, 127.0, 122.5, 122.4, 122.3, 122.2, 122.1, 115.2, 115.1, 77.9, 66.2, 62.6, 62.2, 55.4, 49.0, 48.2, 43.4, 42.1, 38.2, 36.9, 30.3, 30.3, 28.7, 24.4, 23.3, 23.0, 22.5 (as a mixture of rotamers); Mp 112.7-116.2° C.; HRMS (ESI$^+$) m/z calcd for C$_{29}$H$_{38}$N$_5$O$_5$ [M+H] 536.2867, found 536.2867.

tert-butyl (S)-(3-(2-(2-methylpyrrolidin-2-yl)-1H-benzo[d]imidazole-4-carbox-amido)propyl)carbamate. A solution of 12 (500 mg, 0.933 mmol) and 10% Pd/C (99 mg, 0.093 mmol) in MeCOH (5 mL) was placed in the Anton Paar hydrogenator and the reaction mixture was flushed with argon and purged with hydrogen (3×). The pressure was set to 6 bar and the mixture stirred at this pressure at rt overnight. The solution was filtered through a plug of CELITE© and washed with portions of CH$_2$Cl$_2$. The solvent was evaporated and the crude material was purified via chromatography on SiO$_2$ (100% CH$_2$Cl$_2$ to 10% MeOH/CH$_2$Cl$_2$) to give tert-butyl (S)-(3-(2-(2-methylpyrrolidin-2-yl)-1H-benzo[d]imidazole-4-carboxamido)propyl)carbamate as a white foam (375 mg, 85%). $^1$H NMR (600 MHz, DMSO-d$_6$) δ 12.50 (br s, 2H), 9.94 (br s, 1H), 7.78 (d, J=7.5 Hz, 1H), 7.62 (d, J=7.5 Hz, 1H), 7.25 (t, J=7.7 Hz, 1H), 6.92-6.87 (m, 1H), 3.45-3.38 (m, 2H), 3.12-3.04 (m, 3H), 2.93-2.86 (m, 1H), 2.45-2.38 (m, 1H), 1.89-1.80 (m, 2H), 1.72-1.64 (m, 3H), 1.59 (br s, 3H), 1.38 (s, 9H); $^{13}$C-NMR (600 MHz, DMSO-d$_6$) δ 165.3, 156.2, 122.1, 121.8, 79.7, 79.4, 79.2, 77.9, 62.6, 60.2, 55.4, 49.1, 46.4, 38.1, 36.8, 30.4, 28.7, 27.6, 25.7, 21.3, 14.6; IR (ATR, neat) 3269, 2973, 1694, 1645, 1612, 1523, 1406, 1365, 1245, 1166, 1046, 988, 758 cm$^{-1}$; Mp 79.8-83.2° C.; HRMS (ESI$^+$) m/z calcd for C$_{21}$H$_{32}$N$_5$O$_3$ [M+H] 402.2500, found 402.2499.

(S)—N-(3-aminopropyl)-2-(2-methylpyrrolidin-2-yl)-1H-benzo[d]imidazole-4-carboxamide hydrochloride (13). To a solution of tert-Butyl (S)-(3-(2-(2-methylpyrrolidin-2-yl)-1H-benzo[d]imidazole-4-carboxamido)propyl)carbamate (32.8 mg, 0.0817 mmol) in CH$_2$Cl$_2$ (1 mL) was added 4M HCl in dioxane (0.2 mL, 0.8 mmol). The resulting mixture was stirred at rt for 2 h. The desired product was filtered off, washed with portions of hexanes and the resulting white solid (27.1 mg, 98%) was used in the next step without further purification. HRMS (ESI$^+$) m/z calcd for C$_{16}$H$_{24}$N$_5$O [M+H] 302.1975, found 302.1974.

tert-Butyl ((4S,7S,E)-7-benzyl-2-methyl-8-((S)-2-(((S)-3-methyl-1-(((S)-15-(2-((S)-2-methylpyrrolidin-2-yl)-1H-benzo[d]imidazol-4-yl)-3,9,15-trioxo-1-phenyl-2-oxa-4,10,14-triazapentadecan-8-yl)amino)-1-oxobutan-2-yl) carbamoyl)pyrrolidin-I-yl)-8-oxooct-5-en-4-yl)carbamate ("XJB-Veliparib", 15). To a solution of XJB-acid 14 (36.9 mg, 0.0458 mmol) and 13 (23.2 mg, 0.0687 mmol) in DMF (0.92 mL, 0.05M) at 0° C. was added DIPEA (40 μL, 0.23 mmol) followed by the dropwise addition of T$_3$P (50% in DMF, 35 μL, 0.060 mmol). The reaction mixture was stirred at 0° C. for 1 h, after which it was quenched with aq. NH4Cl, and extracted with CH$_2$Cl$_2$ (3×). The combined organic layers were washed with 5% aq. LiCl solution (1×), dried (MgSO$_4$), and evaporated to give the crude product as a pale yellow oil. The residue was purified via chromatography on SiO$_2$ (100% CH$_2$Cl$_2$ to 15% MeOH/CH$_2$Cl$_2$) to afford 15 as a white solid (18.5 mg, 37%). $^1$H NMR (400 MHz, DMSO-d$_6$, 100° C.) δ 9.32 (br s, 1H), 7.88 (d, J=7.44 Hz, 1H), 7.72 (d, J=7.96 Hz, 1H), 7.69-7.59 (m, 1H), 7.47-7.38 (m, 1H), 7.37-7.31 (m, 5H), 7.30-7.26 (m, 1H), 7.25-7.12 (m, 5H), 6.79 (br s, 1H), 6.12 (d, J=7.72 Hz, 1H), 5.52-5.42 (m, 2H), 5.02 (s, 2H), 4.44-4.37 (m, 1H), 4.30-4.23 (m, 1H), 4.18-4.09 (m, 1H), 3.93-3.84 (m, 1H), 3.53-3.35 (m, 6H), 3.29-3.21 (m, 3H), 3.10-3.03 (m, 4H), 2.72-2.00 (m, 3H), 1.98-1.88 (m, 2H), 1.84 (br s, 3H), 1.80-1.71 (m, 5H), 1.66-1.57 (m, 1H), 1.55-1.43 (m, 3H), 1.38 (s, 9H), 1.30-1.25 (m, 4H), 0.90-0.78 (m, 12H); $^{13}$C NMR (700 MHz, DMSO-$d_6$) δ 172.7, 172.5, 172.2, 171.9, 171.8, 171.7, 171.4, 171.3, 171.2, 164.8, 156.6, 155.3, 155.2, 139.7, 139.5, 137.7, 135.0, 134.6, 129.6, 128.8, 128.4, 128.3, 128.2, 127.8, 126.4, 126.2, 122.8, 78.0, 77.8, 65.6, 64.9, 64.6, 59.7, 59.6, 59.3, 58.2, 53.1, 53.0, 50.7, 50.5, 49.3, 48.8, 47.2, 47.1, 45.5, 38.9, 38.2, 36.5, 36.4, 35.2, 32.4, 30.9, 30.7, 30.2, 29.8, 28.7, 26.5, 25.0, 24.7, 24.4, 24.3, 23.8, 23.0, 22.8; Mp 147.2-152.6° C.; IR (ATR, $CH_2Cl_2$) 3291.7, 2955.8, 1647.1, 1528.8, 1439.1, 1365.7, 1248.0, 1167.2, 1028.3, 758.2, 698.1 cm$^{-1}$; HRMS (ESI) m/z calcd for $C_{60}H_{85}N_{10}O_9$ 1089.6496, found 1089.6495.

PARP1 Activity: The capacity to inhibit PARP1 was determined using a commercial assay (Trevigen, Gaithersburg, Md.) as per manufacturer's direction. Various concentrations of XJB-Veliparib or naked veliparib were added to histone-coated wells containing active PARP1 enzyme and NAD$^+$ in surplus.

Quantification of XJB-veliparib: The mitochondrial fraction (50 μL) or nuclear fraction (50 μL), treated with XJB-veliparib or veliparib (100 nM), was added to a 5:1 ratio of $CH_2Cl_2$:MeOH (950 μL) and vortexed (30 sec). Water (150 μL) was added and the solution was vortexed (15 sec) and set aside to equilibrate at room temperature (30 min). The resulting suspension was placed in an Eppendorf Centrifuge 5702 (4400 rpm, 20° C.) for 12 min. The organic layer was extracted and filtered through a 0.45 μm filter for analysis.

XJB-Veliparib and veliparib content was quantified on a Thermo Scientific Exactive Orbitrap LC-MS (ESI positive ion mode) coupled to a Thermo Scientific Accela HPLC system using a 3.5 μM Water XTerra C18 column (2.1×50 mm; 20 min gradient elution with MeCN/$H_2O$ containing 0.1% formic acid at a flow rate of 500 μL/min from 5:95 at 0-1.0 min to 95:5 at 12.0 min, back to 5:95 from 16.0 to 16.1 min). Calibration curves for XJB-Veliparib and veliparib were run in duplicate from 102 nM to 5.7 nM. Samples (10 μL) were injected in triplicate and Thermo Xcalibur software was used to determine the concentration of XJB-Veliparib and veliparib in mitochondrial and nuclear fractions (n=3). The concentration was reported as pM concentration of XJB-Veliparib per 10 μg of protein with corresponding standard deviation values.

Cell Cultures: Primary cortical neuron-enriched cultures were prepared from 16-17 day old Sprague-Dawley rat embryos. Dissociated cell suspensions were filtered through a 70 μm nylon cell strainer and seeded in 96-well plates (5×10$^4$ cells/well) or on poly-D-lysine coated glass coverslips, and maintained in Neurobasal medium with B27 supplements (Life Technologies, Carlsbad, Calif.). Experiments were performed 12 days in vitro (DIV).

HT22 cells were cultured at 37° C. in Dulbecco's modified Eagle's medium (DMEM) (Invitrogen Inc., Carlsbad, Calif.) supplemented with 10% fetal bovine serum (FBS) (Thermo Fisher Scientific, San Jose, Calif.) and 1% penicillin-streptomycin (ATCC, Manassas, Va.) in an atmosphere containing 5% $CO_2$. Cells were cultured for 24 to 48 hr before use.

Oxygen-glucose Deprivation: To model ischemia-reperfusion in vitro, culture medium was replaced with a pre-equilibrated low glucose (0.5 mM) medium. Neurons were transferred into a sealed hypoxic chamber (Coy Laboratory Products Inc., Grass Lake, Mich.) set to an atmosphere of 95% $N_2$ with 5% $CO_2$ at 37° C. for 2 h. After OGD neurons were removed from the chamber and returned to the incubator.

Excitotoxicity: To model excitotoxicity in primary cortical neurons, cells were exposed to 10 μM L-glutamate with 10 μM glycine. Neuronal cells from HT22 cell line were exposed to 5 mM L-glutamate.

Assessment of Cell Death: Cell death was quantified by measuring lactate dehydrogenase (LDH) released into supernatant using a colorometric assay. LDH values were normalized to 100% cell death caused by 0.5% Triton X-100 exposure. Data are reported as the percentage of dead cells relative to total cells and presented as mean±standard deviation (SD).

Immunocytochemistry and Immunofluorescent Microscopy: Neurons grown on poly-D-lysine coated glass coverslips were fixed in 2% paraformaldehyde and permeabilized with TritonX-100. Coverslips were then incubated in a 1:200 dilution of mouse monoclonal antibody against PAR (SA216, ENzo Life Sciences, Inc., Farmingdale, N.Y.) and an antibody against TOMM20 (Abcam, Cambridge, Mass.) followed by incubation in the appropriate secondary antibodies. Cell nuclei were labelled with 4',6 diamidino-2-phenylindole (DAPI) for standard confocal microscopy or DRAQ5 (both from ThermoFisher Scientific, Waltham, Mass.) for STED microscopy. Images were collected using an Olympus Fluoview 1000 confocal microscope (Olympus Corporation of the Americas, Center Valley, Pa.).

For STED imaging a Leica TCS SP8 super resolution STED microscope with a pulsed white light laser and AOBS detection system was used (Leica Microsystems, Wetzlar, Germany). Images were collected using the 775 nm STED laser line with 30% 3D STED using the Leica STED WHITE oil objective lens (HC PL APO 100×/1.40 OIL) with a 200 Hz scan speed and 2× line averaging. Pixel size was set to 45 nm/pixel, step size was set to 160 μm, and pinhole was set at 132.8 μm (0.875 AU). TOMM20 was visualized using Alexa Fluor 555, exciting at 553 nm and detecting between 558-599 nm and temporally gate between 0.83-4.33 nm. PAR was visualized with Alexa Fluor 594, exciting at 598 nm and detecting between 603-666 nm and temporally gated between 0.3-6.0 nsec. DRAQ5 (ThermoFisher Scientific, Waltham, Mass.) was excited at 662 and detected between 667 to 780 nm and temporally gated between 0.3-6.0 nsec. Channels were collected between stacks, sequentially.

Figure 4:
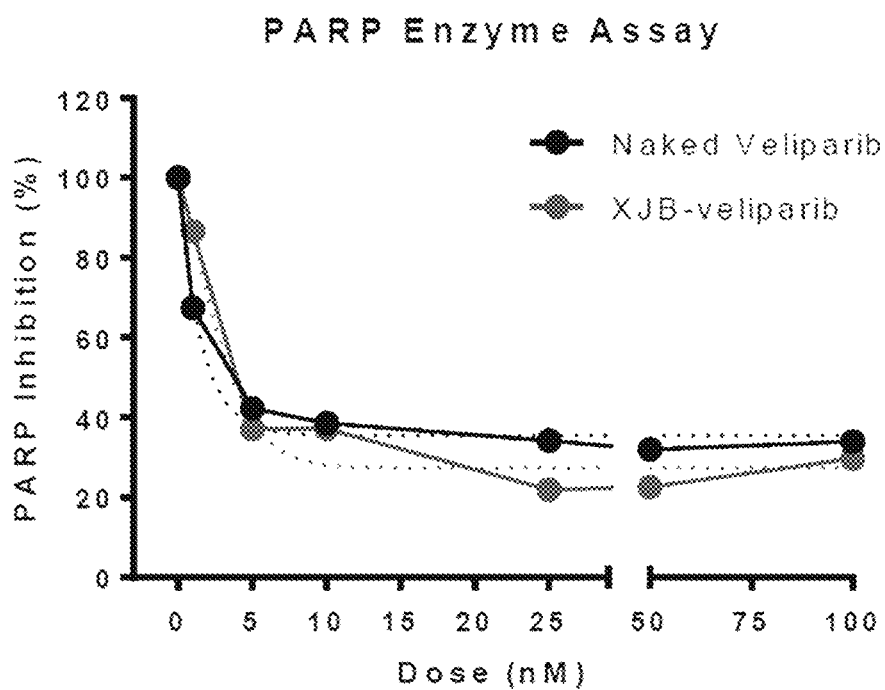
FIG. 4. Capacity of 15 to inhibit PARP-1 enzyme. Performed in triplicate.

PARP Inhibition ex vivo, Cytotoxicity, and Mitochondrial Enrichment Studies: To determine whether the linkage to the mitochondria-targeting moiety on 15 affected PARP1 inhibition, a control assay with active PARP1 enzyme was used. PARP1 inhibition was similar between untargeted veliparib and the XJB-veliparib conjugate 15 (FIG. 4; experiments performed in triplicate), and is consistent with the reported $K_i$ of veliparib of 5.2 nmol/L.

Figure 5:
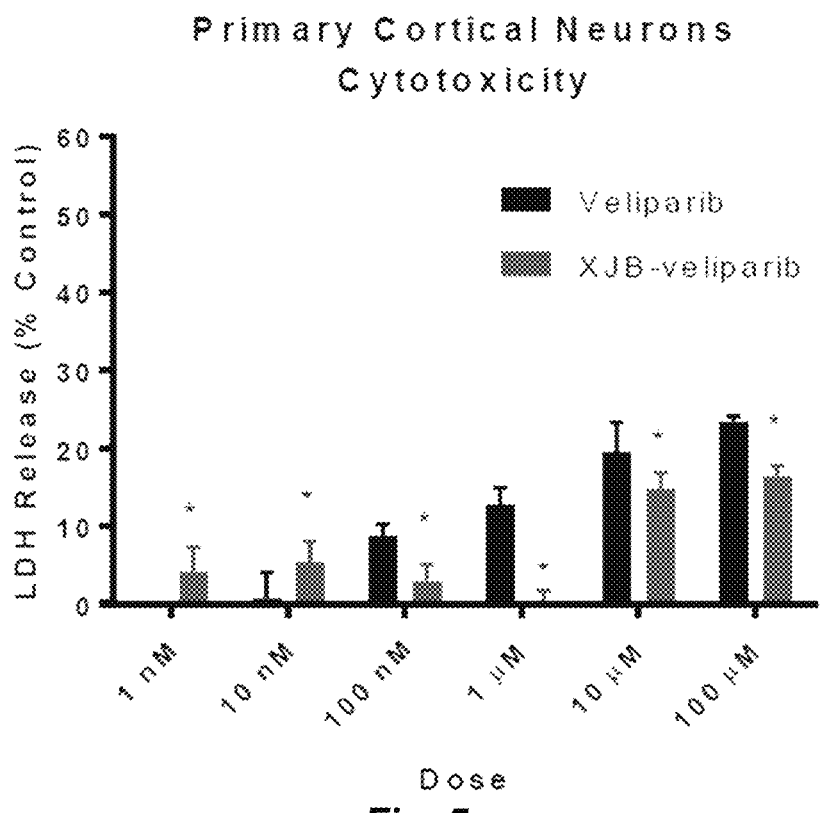
FIG. 5. Cytotoxicity studies in rat primary cortical neurons. LDH release was measured at 24 h (n=6/group).

To investigate the biological properties and potential cytotoxicity of XJB-veliparib, rat primary cortical neurons were exposed to varying concentrations of untargeted veliparib and XJB-veliparib. Cytotoxicity was assessed by LDH release from dying neurons at 24 h. While both veliparib and XJB-veliparib showed a dose-dependent cytotoxicity profile, XJB-veliparib was significantly less toxic compared with unconjugated veliparib (FIG. 5; n=6/group; *P<0.05). Neurotoxicity defined as >10% cell death was seen with veliparib at 1 μM concentration, vs. a 10 μM concentration required for XJB-veliparib. Significant cytotoxicity has previously been reported when leukemia cells are exposed to micromolar concentrations of veliparib. Since cytotoxicity produced by PARP inhibitors in clinical use, including veliparib, may be related to genomic instability, mitochondria-targeting PARP inhibitors may have a therapeutic advantage where prevention of cell death is desired.

Figure 6A:
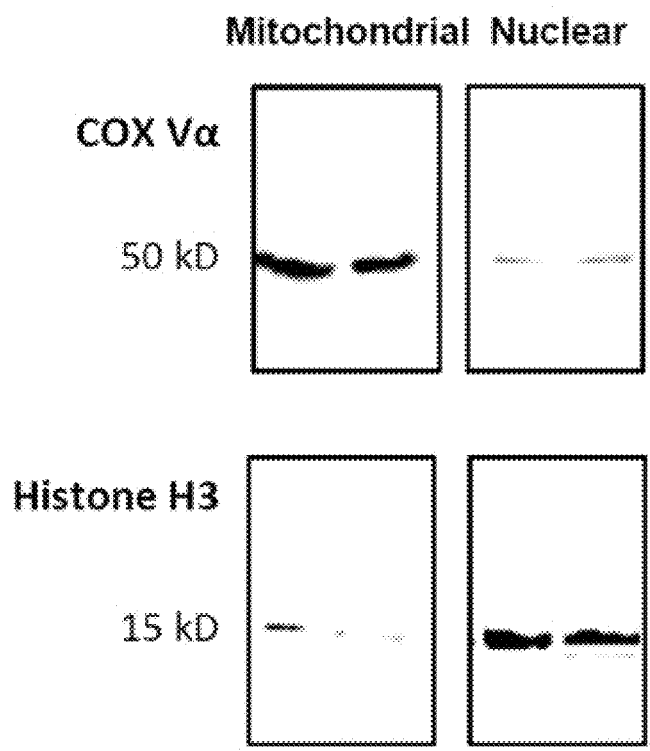
FIGS. 6A-6C. Mitochondrial enrichment of XJB-veliparib.
Figure 6B:
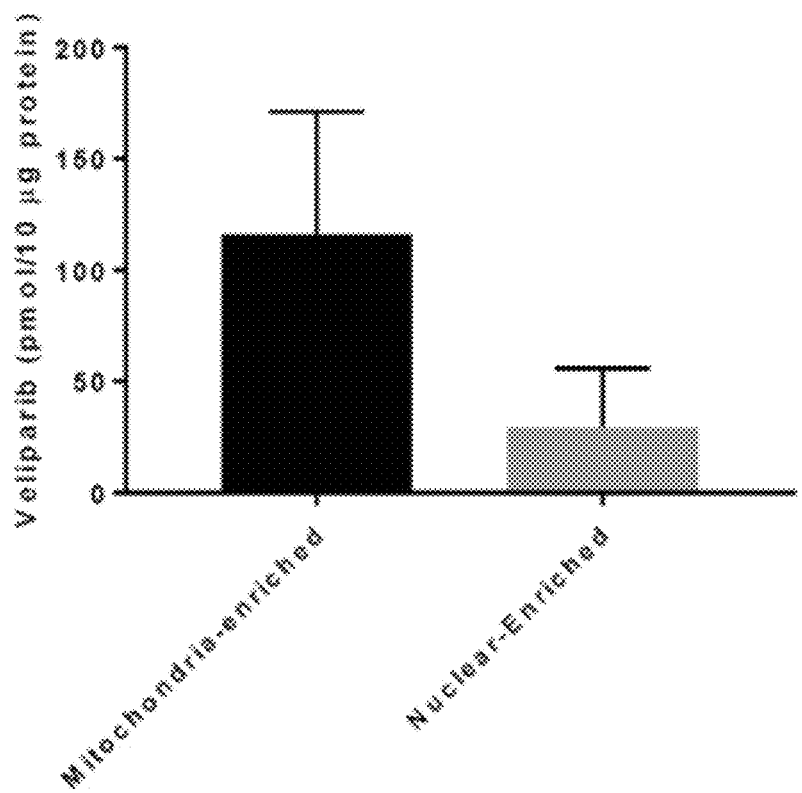
Figure 6C:
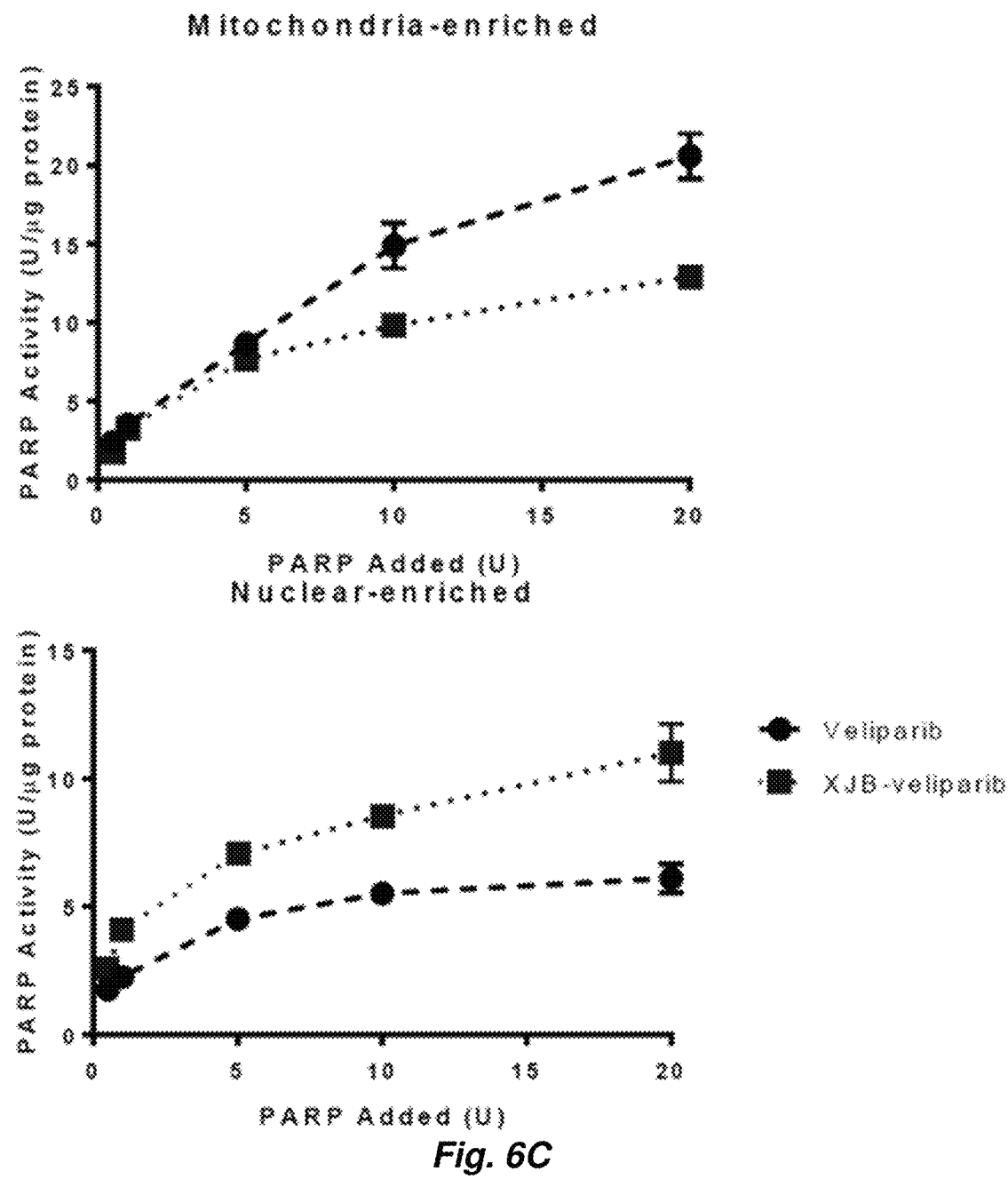

To verify mitochondrial enrichment, rat primary cortical neurons were exposed to 100 nM XJB-veliparib for 24 h. Mitochondria- and nuclear-enriched subcellular fractions were obtained and verified by western blot using antibodies against the cytochrome oxidase subunit Vα (COX Vα) and histone H3, respectively (FIG. 6A). In mitochondria-enriched fractions, the LCMS analysis of XJB-veliparib indicated a concentration of 116±55 pmol/10 μg protein compared with 29±27 pmol/10 μg protein in nuclear-enriched fractions (FIG. 6B; mean±standard deviation [SD]; n=3 independent experiments). In addition, mitochondria-enriched fractions spiked with active PARP1 enzyme showed greater PARP1 inhibitory capacity compared to unconjugated veliparib (FIG. 6C; performed in triplicate).

Figure 7A:
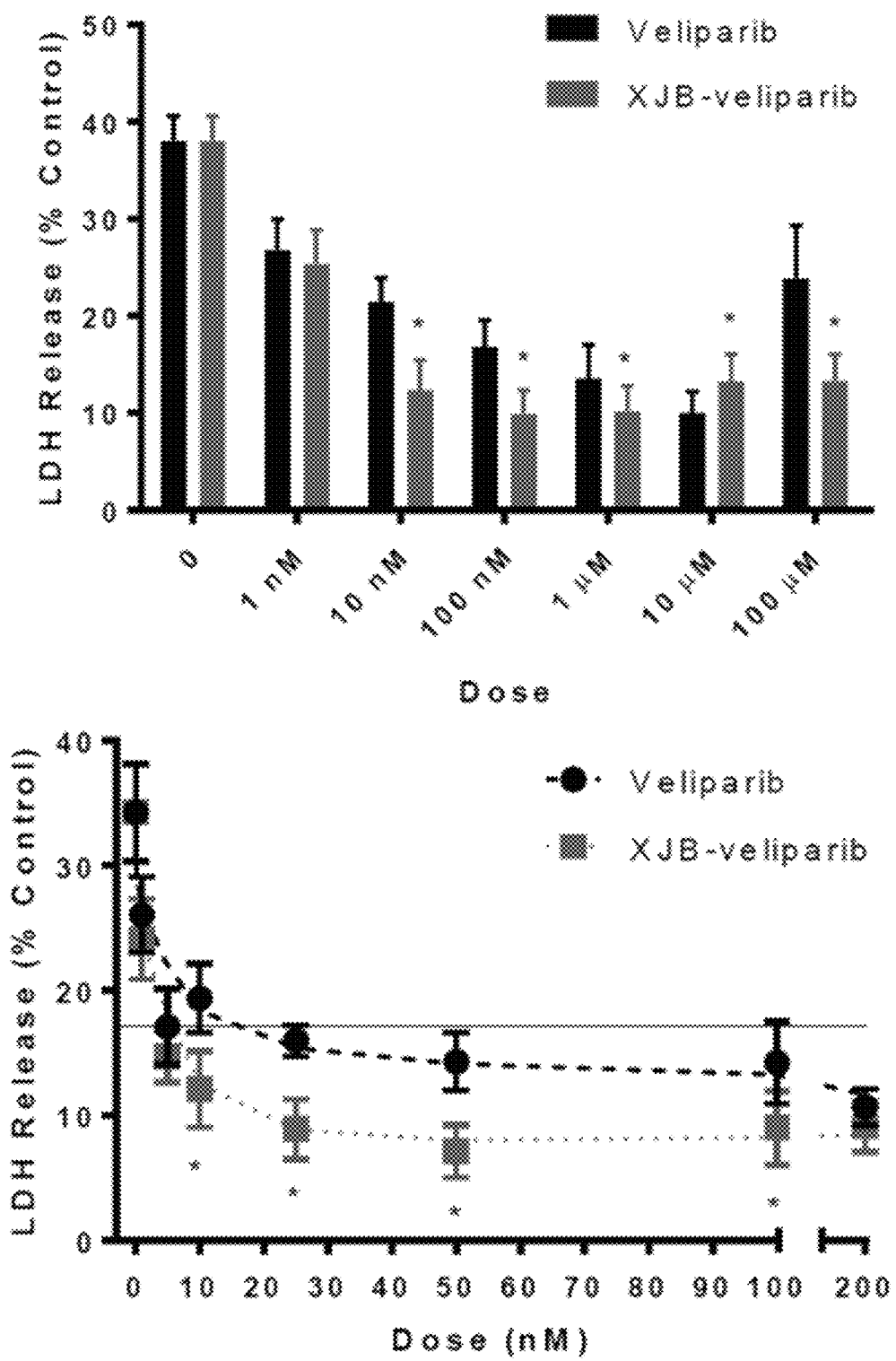
FIG. 7A-7C.

XJB-veliparib Neuroprotection Studies: To determine whether mitochondria-targeting XJB-veliparib can promote neuronal survival in ischemia-like conditions in vitro, primary cortical neurons at 12 DIV were subjected to OGD. Cultured neurons were exposed to a hypoxic and glucose-depleted environment for 2 h, followed by normal culture conditions for 24 h to mimic ischemia/reperfusion injury. As shown in FIG. 7A, treatment with XJB-veliparib significantly attenuated OGD-induced cell death at low nanomolar concentrations. Specifically, 10 nM XJB-veliparib reduced cell death by 67% (LDH release 12.4±3.1% vs. 38.0±2.5%, 10 nM XJB-veliparib vs. vehicle; mean±SD; P<0.05). Treatment with concentrations >100 nM of either veliparib or XJB-veliparib conjugate provided no additional protection. Both XJB-veliparib and non-targeting veliparib appear more protective against OGD compared with other published PARP1 inhibitors, where protection is observed in micromolar ranges. In vivo, PARP1 inhibition is highly effective at reducing neuronal death caused by ischemia-reperfusion injury.

Figure 7B:
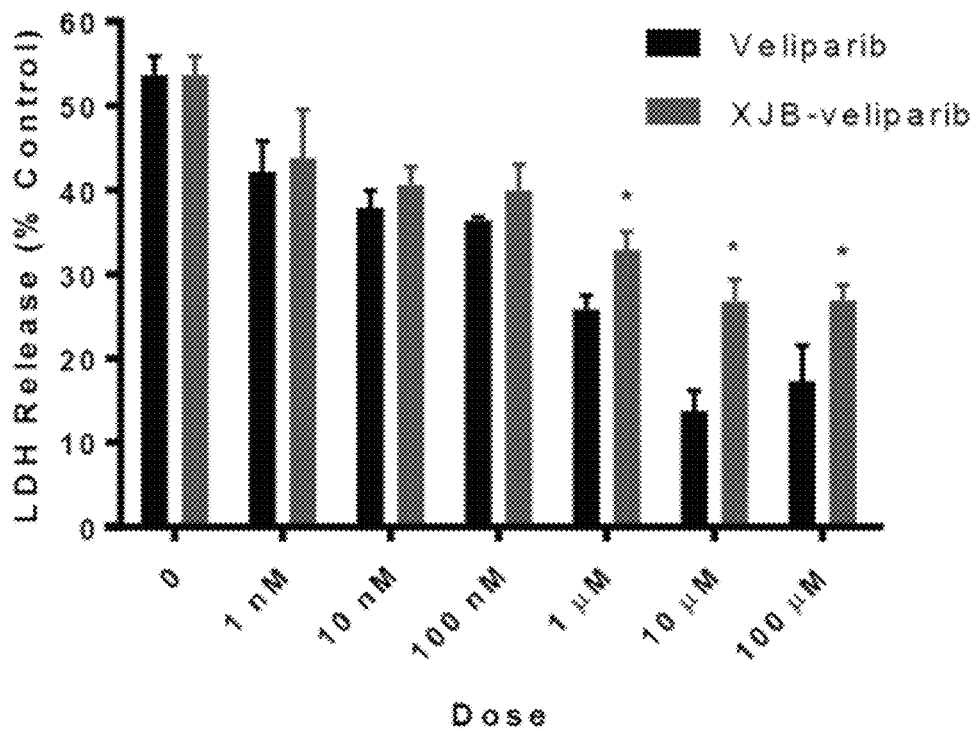

To determine whether XJB-veliparib was also effective in attenuating excitotoxic cell death in vitro, primary cortical neurons were exposed to 10 μM L-glutamate and 10 μM glycine with varying concentrations of XJB-veliparib or naked veliparib for 24 h. PARP inhibition reduced cell death after glutamate/glycine exposure in a dose-dependent manner (FIG. 7B). Differing from in vitro ischemia/reperfusion, non-targeting veliparib was more potent than XJB-veliparib in reducing LDH release. This is consistent with previous studies showing an important role for nuclear PARP1 activation in inhibiting excitotoxic neuronal death in vitro (Zhang, J., et al., Nitric oxide activation of poly(ADP-ribose) synthetase in neurotoxicity. Science 1994, 263 (5147), 687-9). In vivo, PARP1 inhibition is effective at reducing N-methyl-D-aspartate (NMDA) but not non-NMDA excitotoxicity (Mandir, A. S., et al., NMDA but not non-NMDA excitotoxicity is mediated by Poly(ADP-ribose) polymerase. J Neurosci 2000, 20 (21), 8005-11).

Figure 7C:
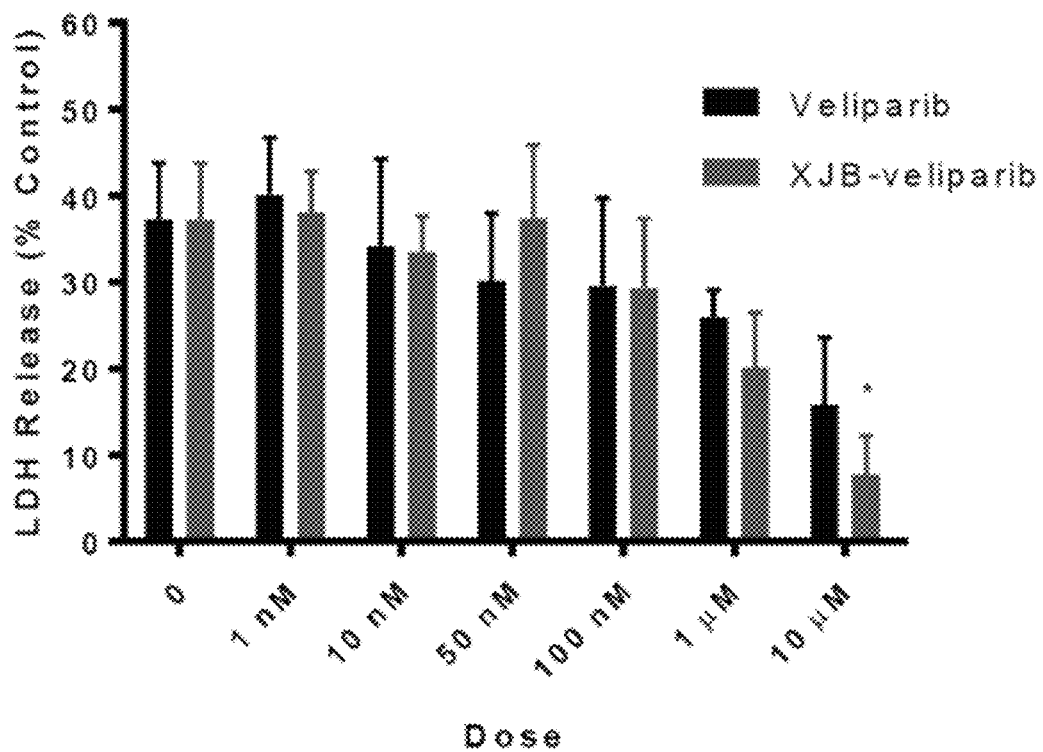

In addition to rat primary cortical neuron cultures, the effect of veliparib and XJB-veliparib was determined in a stable mouse hippocampal neuronal cell line HT22, in which ferroptotic cell death is induced by high concentrations of glutamate. HT22 cells grown to confluence were exposed to 5 mM glutamate and various concentrations of veliparib or XJB-veliparib with LDH release measured at 24 h (FIG. 7C). Both veliparib and XJB-veliparib inhibit glutamate-induced ferroptosis in HT22 cells, with XJB-veliparib slightly more effective than veliparib at higher concentrations (10 μM).

Figure 8:
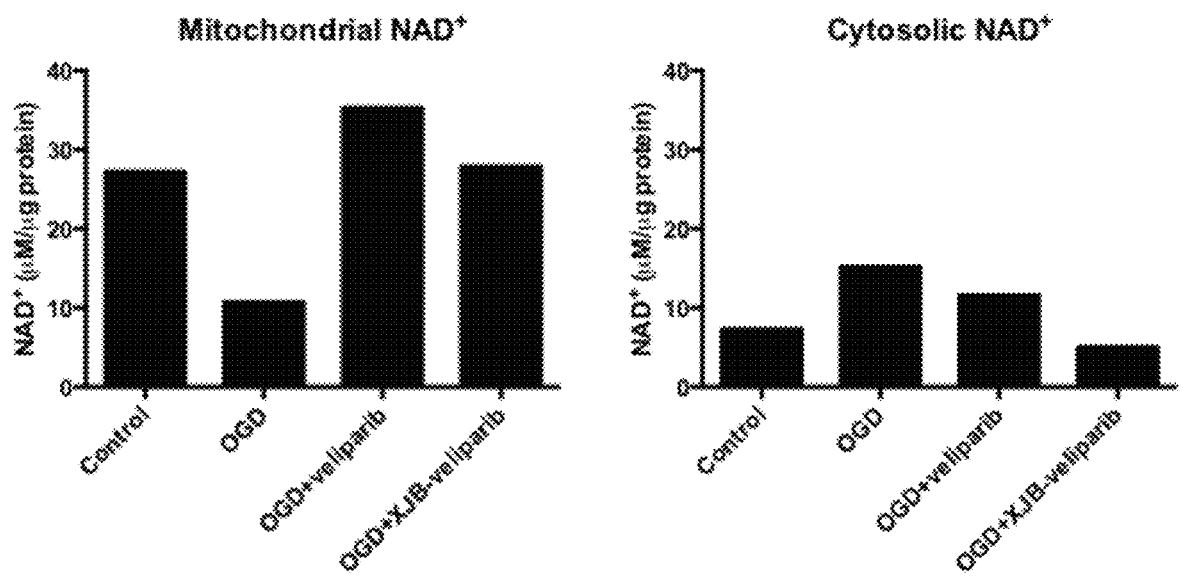
FIG. 8. Mitochondrial and cytosolic $NAD^+$ concentration in primary cortical neurons after OGD. Veliparib and XJB-Veliparib administered at 10 nM dose before OGD. $NAD_+$ concentration measured 24 h after OGD. Assay performed in duplicate.

In order to investigate the cellular site of action of both veliparib and XJB-veliparib, the $NAD^+$ concentrations in mitochondria- and cytosol-enriched fractions were measured after OGD. Both XJB-veliparib and non-targeting veliparib preserve mitochondrial $NAD^+$ stores (FIG. 8). However, while OGD led to increased cytosolic $NAD^+$ levels, it was found that a 10 nM dose of XJB-veliparib prevented efflux of $NAD^+$ from the mitochondria to the cytosol 24 h after OGD.

Figure 9:
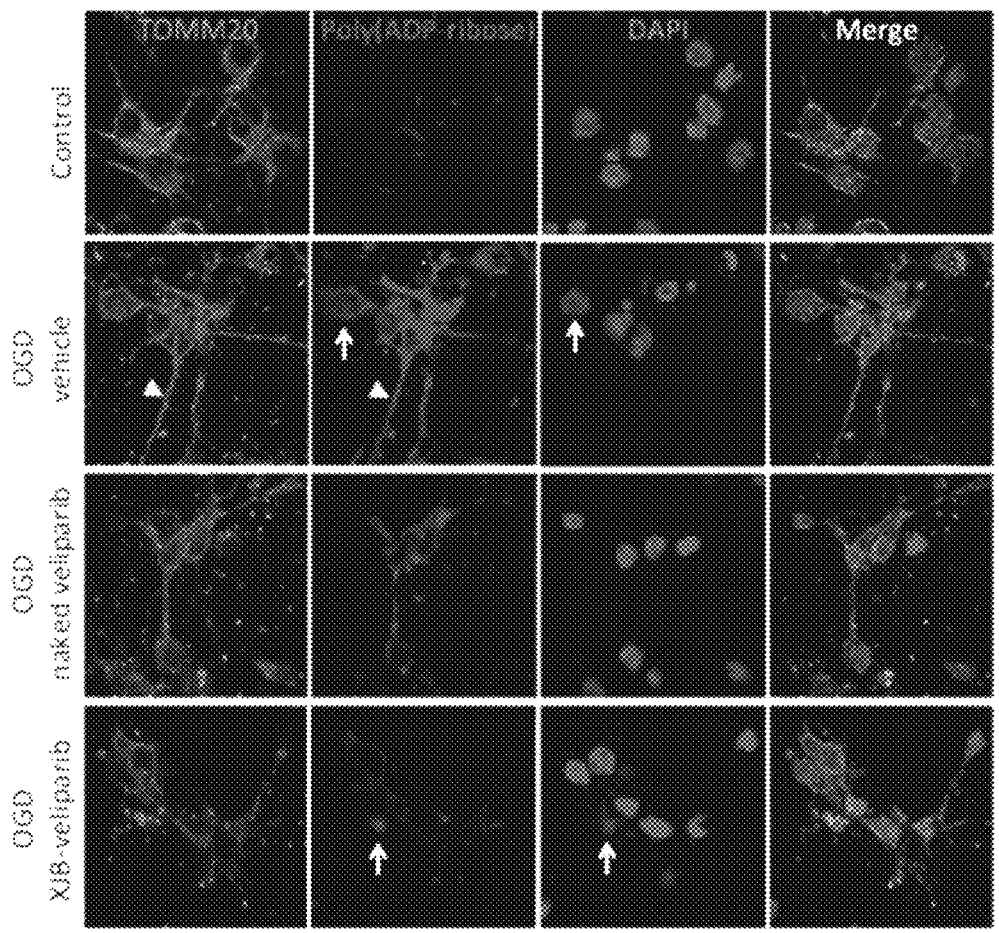
FIG. 9. Mitochondria were labelled with anti-TOMM20 antibody (green), PADPRp were labelled with anti-PAR antibody (red in original), and nuclei were labelled with (DAPI; blue in original). Both mitochondrial (arrowheads) and nuclear (arrows) PADPRp staining were observed. PARP inhibitors were administered at 10 nM doses before OGD and immunohistochemistry was performed 24 h after OGD.

Cellular Localization of Poly(ADP-ribose) Polymers: The cellular localization of poly(ADP-ribose) (PAR) polymers, a footprint of PARP activation, was examined in primary cortical neurons after OGD using immunohistochemistry and confocal microscopy. Primary rat cortical neurons were treated with 10 nM XJB-veliparib, 10 nM veliparib, or vehicle and then exposed to OGD for 2 h. As shown in FIG. 9, one hour after OGD in vehicle treated neurons, PARP activation, assessed by immunofluorescence staining with anti-PAR antibody, was increased in mitochondria (labelled with translocase of outer mitochondrial membrane 20 [TOMM20]) and nuclei (labelled with 4,6-diamidino-2-phenylindole [DAPI]) compared with control neurons (no ischemia; performed in triplicate). After treatment with either veliparib or XJB-veliparib, a reduction of PAR immunofluorescence was observed. The PAR data obtained were consistent with PARP activation in mitochondria after OGD, inhibited by the XJB-veliparib conjugate and the unconjugated veliparib. The relative increase in PAR immunoreactivity observed in mitochondria vs. nuclei in neurons after OGD may be explainable by more effective PAR metabolism by poly(ADP-ribose) glycohydrolase in cell nuclei vs. ADP-ribosylhydrolase 3 in mitochondria.

Figure 10:
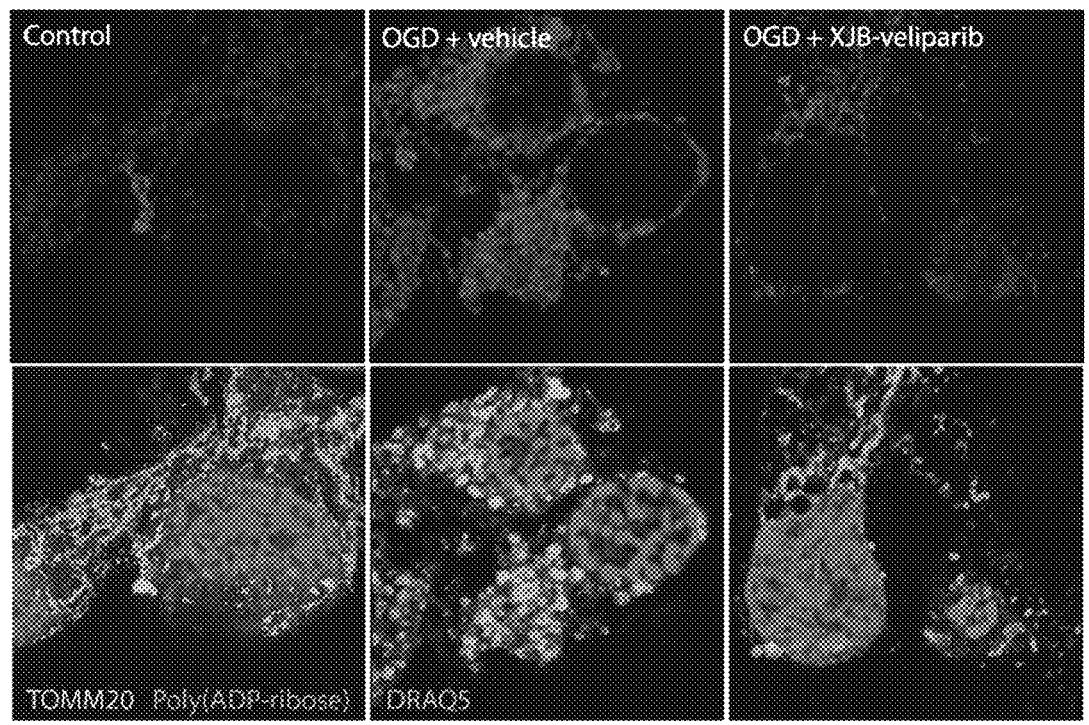
FIG. 10. Mitochondria were labelled with anti-TOMM20 antibody (green), PADPRp were labelled with anti-PAR antibody (red in original), and nuclei were labelled with DRAQ5 (blue in original). Both mitochondrial (arrowheads) and nuclear (arrows) PADPRp staining were observed. PARP inhibitors were administered at 10 nM doses before OGD and immunohistochemistry was performed 24 h after OGD.

To evaluate the impact of XJB-veliparib on mitochondrial structure after OGD, we used stimulation emission depletion (STED) microscopy and immunohistochemistry. Primary rat cortical neurons were treated with 10 nM XJB-veliparib or vehicle and then exposed to OGD for 2 h. Vehicle treated neurons showed increased PARP activation at 1 h as determined by PAR immunohistochemistry, and swollen, circular mitochondria consistent with fission compared with control (no ischemia) neurons (FIG. 10; performed in triplicate). In contrast, PAR immunoreactivity was reduced in neurons treated with XJB-veliparib (vs. vehicle) and mitochondrial architecture appeared partially preserved.

Example 2—XJB-Veliparib Mitigates the Effects of Radiation Exposure

Figure 11:
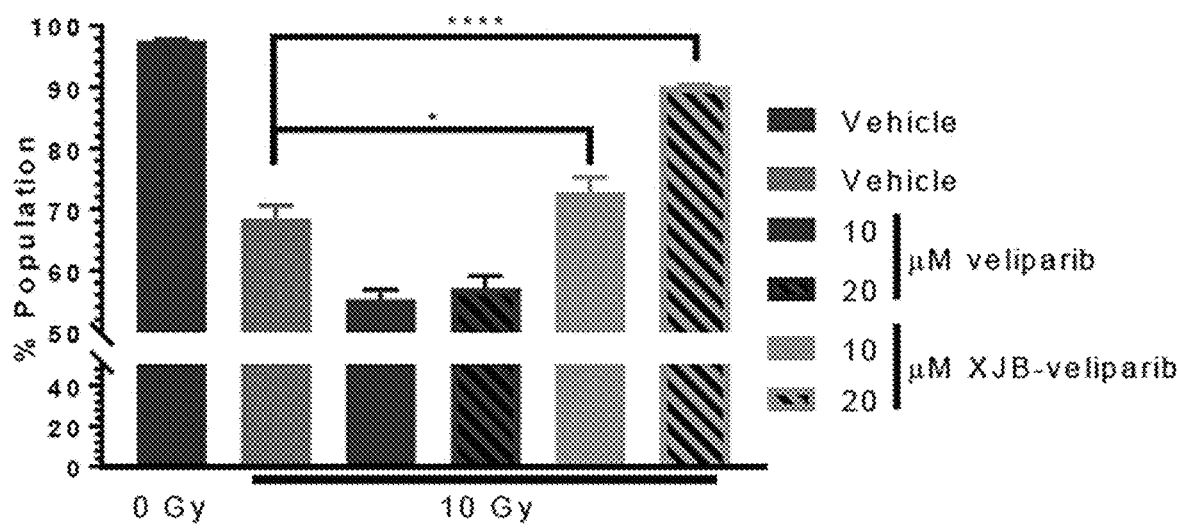
FIG. 11. Graph illustrating that XJB-Veliparib reduces MEF IR-induced cell death.

XJB-veliparib reduces IR-induced cell death and mitochondrial DNA (mtDNA) damage in mouse embryo fibroblasts (MEF), suggesting that XJB-veliparib may be an effective mitigator of radiation toxicity. FIG. 11 shows that XJB-Veliparib reduces irradiation death in MEFs. MEF cells were treated with 10, 20 μM XJB-veliparib for 30 min prior to 10 Gy IR (309R/min, Cs137 source), media was changed to drugless media 4 h post-IR. Survival was assessed at 48 h by Annexin V-FTIC/PI flow cytometry. MEFs treated with XJB-veliparib had increased survival vs. vehicle or veliparib (90.1%±0.3 vs. 68.4%±2.2 or 57.1%±0.1.9, respectively). Mean±SD, *$p<0.05$, ****$p<0.0001$.

Figure 12:
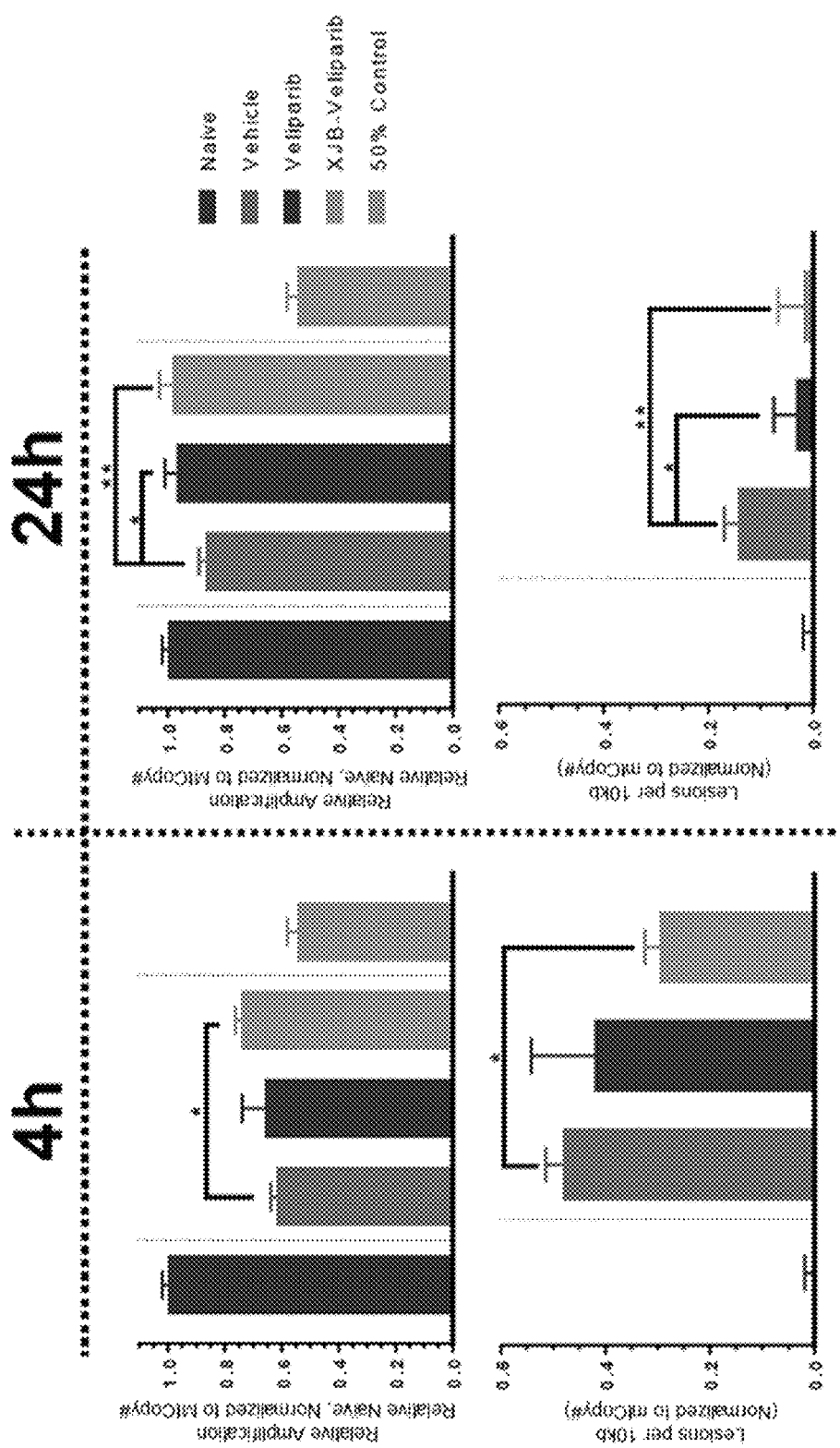
FIG. 12. Graphs showing that XJB-veliparib reduces γ-irradiation-induced mitochondrial DNA damage.

FIG. 12 shows that XJB-veliparib reduces γ-irradiation-induced mitochondrial DNA damage in MEFs. PARylation of mtDNA repair enzymes, polymerase-γ and exo/endonuclease G, by mt-PARP1 is thought interfere with normal mtDNA repair. MEFs were treated with 20 μM XJB-veliparib or unconjugated veliparib for 30 minutes prior to 10 Gy IR (309R/min, Cs137 source), media was changed to drugless media 4 h post-IR. Cells were harvested and DNA extracted 4 and 24 h post-IR. Specific inhibition of mt-PARP1 by XJB-veliparib reduced the number of PCR-detectable mtDNA lesions (increased qPCR amplification efficiency) following γ-IR compared to vehicle-treated (0.30±0.03 vs. 0.48±0.03, respectively). Veliparib had no effect compared to vehicle irradiated cells. ANOVA, *p<0.05, **p<0.01.

The following numbered clauses describe non-limiting various aspects of the present invention.

1. A compound comprising a mitochondria-targeting gramicidin S peptide isostere moiety covalently linked to a PARP inhibitor, or a pharmaceutically-acceptable salt or ester thereof.

2. The compound of clause 1, having the structure:

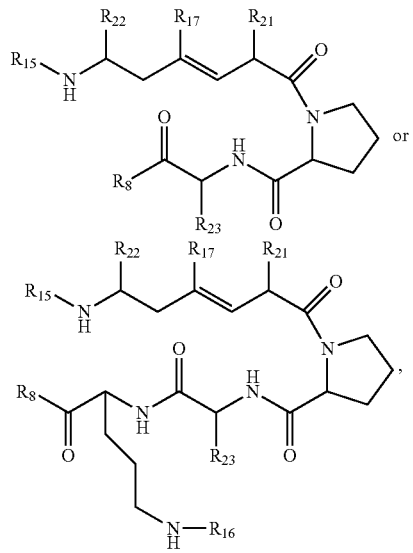

wherein $R_8$ is —NH—$R_9$, —O—$R_9$, —CH$_2$—$R_9$, -L-$R_9$, —NH-L-$R_9$, or —O-L-$R_9$, where $R_9$ is a PARP inhibitor, such as, olaparib, veliparib, CEP-8983 (II-methoxy-4,5,6,7-tetrahydro-IH-cyclopenta[a]pyrrolo[3,4-c]carbazole-I,3(2H)-dione) or a prodrug thereof (e.g. CEP-9722), rucaparib, E7016 (10-((4-hydroxypiperidin-I-yl)methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H]phenanthridinone, PD128763, and analogues, isosteres, and derivatives thereof, and where L is a $C_{1-5}$ alkyl linker, optionally comprising an ester or amide linkage;

$R_{15}$ and $R_{16}$, independently are an amine protecting group or acylated;

$R_{21}$ is H or $C_{1-3}$ alkylaryl, such as methylphenyl (—CH$_2$-Ph);

$R_{22}$ and $R_{23}$ are, independently, H, $C_{1-4}$alkyl or heterosubstituted alkyl, such as a thioether, for example and without limitation, an aliphatic amino acid side chain, such as

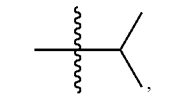
(Val, V)

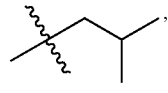
(Leu, L)

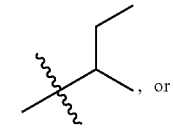
(Ile, I)
, or

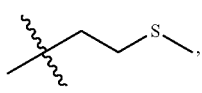
(Met, M)

or a pharmaceutically acceptable salt or ester thereof.

3. The compound of clause 2, having the structure:

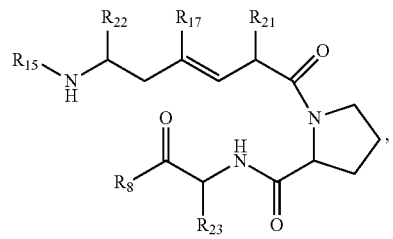

or a pharmaceutically acceptable salt or ester thereof.

4. The compound of clause 2, having the structure:

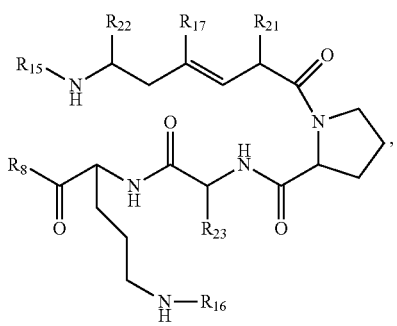

or a pharmaceutically acceptable salt or ester thereof.

5. The compound of any one of clauses 2-4, wherein $R_{22}$ and $R_{23}$ are, independently, aliphatic amino acid side chains, such as

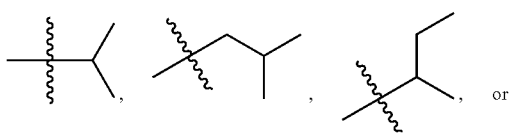

-continued

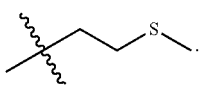

6. The compound of clause 2, having the structure:

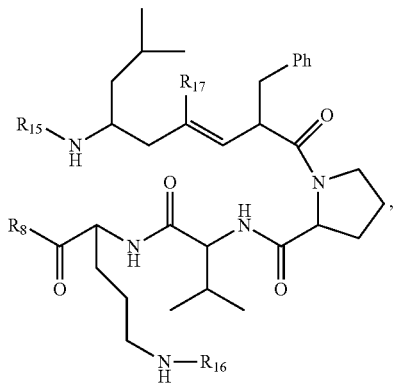

or a pharmaceutically acceptable salt or ester thereof.

7. The compound of any one of clauses 2-6, wherein $R_{15}$ is Boc and $R_{16}$, when present, is Cbz.

8. The compound of clause 2, having the structure:

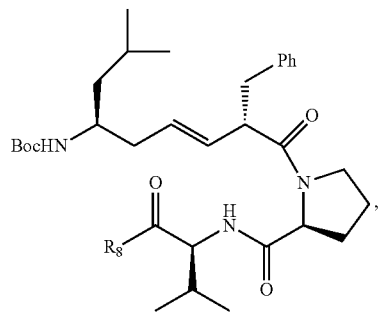

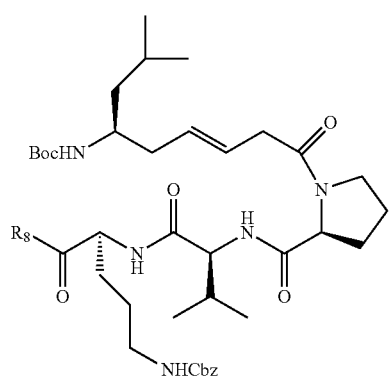

pharmaceutically-acceptable salt or ester thereof.

9. The compound of any one of clauses 2-8, wherein $R_8$ is:

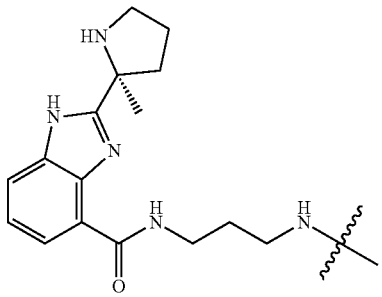 [SMILES: *NCCCNC(=O)c1cccc2[nH]c([C@]3(C)CCCN3)nc12]

or a pharmaceutically-acceptable salt or ester thereof.

10. The compound of clause 1, having a structure:

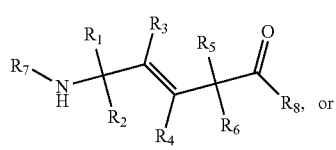
(I)

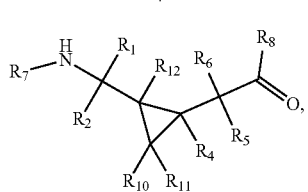
(II)

wherein $R_1$, $R_2$, $R_5$, and $R_6$ are independently hydrogen, hydroxyl, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted, for example, and without limitation, $R_1$, $R_2$, $R_5$, and $R_6$ are independently methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl, or hydroxyphenyl;

$R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_7$ is —C(O)—$R_{13}$, —C(O)O—$R_{13}$, or —P(O)—($R_{13}$)$_2$, wherein $R_{24}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_7$ is Ac (Acetyl, R=—C(O)—CH$_3$), Boc (R=—C(O)O-tert-butyl), Cbz (R=—C(O)O-benzyl (Bn)), or a diphenylphosphate group;

$R_8$ is —NH—$R_9$, —O—$R_9$, —CH$_2$—$R_9$, -L-$R_9$, —NH-L-$R_9$, or —O-L-$R_9$, where $R_9$ is a PARP inhibitor or a derivative or isostere thereof, and where L is a $C_{1-5}$ alkyl linker, optionally comprising an ester or amide linkage;

R$_3$ is a halo, a C$_1$-C$_6$ straight or branched-chain alkyl or a C$_1$-C$_6$ straight or branched-chain alkyl further comprising one or more (C$_6$H$_5$) groups that are independently unsubstituted, or methyl-, ethyl-, hydroxyl- or halo-substituted; and R$_{10}$, R$_{11}$, and R$_{12}$ are independently H or a halo;

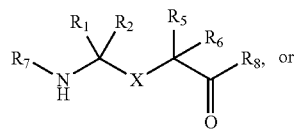
(III)

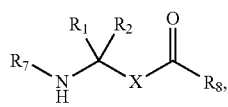
(IV)

wherein X is

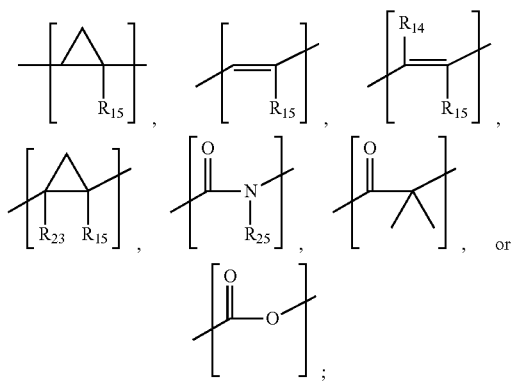
;

R$_1$, R$_2$, R$_5$, R$_6$, and R$_{14}$ are each independently hydrogen, halo, a C$_1$-C$_6$ straight or branched-chain alkyl, or a C$_1$-C$_6$ straight or branched-chain alkyl further comprising a phenyl (C$_6$H$_5$) group, wherein the C$_1$-C$_6$ straight or branched-chain alkyl group or the C$_1$-C$_6$ straight or branched-chain alkyl group comprising a phenyl group is unsubstituted or is methyl-, hydroxyl- or halo-substituted;

R$_8$ is —NH-R$_9$, —O—R$_9$, —CH$_2$—R$_9$, -L-R$_9$, —NH-L-R$_9$, or —O-L-R$_9$, where R$_9$ is a PARP inhibitor or a derivative or isostere thereof, and where L is a C$_1$-5 alkyl linker, optionally comprising an ester or amide linkage; and R$_7$ is —C(O)—R$_{13}$, —C(O)O—R$_{13}$, or —P(O)—(R$_{13}$)$_2$, wherein R$_{13}$ is C$_1$-C$_6$ straight or branched-chain alkyl or a C$_1$-C$_6$ straight or branched-chain alkyl optionally comprising one or more (C$_6$H$_5$) groups that are independently unsubstituted, or methyl-, ethyl-, hydroxyl-, halo-substituted or fluoro-substituted, for example and without limitation, R$_{13}$ is Ac (Acetyl, R=—C(O)—CH$_3$), Boc (R=—C(O)O-tert-butyl), Cbz (R=—C(O)O-benzyl (Bn)), or a diphenylphosphate group; or (V)

[Structure V shown]

wherein R$_8$ is —NH—R$_9$, —O—R$_9$, —CH$_2$—R$_9$, -L-R$_9$, —NH-L-R$_9$, or —O-L-R$_9$, where R$_9$ is a PARP inhibitor or a derivative or isostere thereof, and where L is a C$_{1-5}$ alkyl linker, optionally comprising an ester or amide linkage; R$_{15}$ and R$_{16}$, independently are an amine protecting group or acylated. In one aspect, R$_{15}$ and R$_{16}$ are protecting groups independently selected from the group consisting of: 9-fluorenylmethyloxycarbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT), and R$_{17}$ is H or methyl, optionally, R$_{15}$ is Boc and R$_{16}$ is Cbz.

11. The compound of clause 10, having the structure of (I) or (II).

12. The compound of clause 10, having the structure of (III) or (IV).

13. The compound of clause 10, having the structure of (V).

14. The compound of clause 1, having the structure:

[Structure shown with BocHN, Ph, R$_{17}$, R$_8$, NHCbz substituents]

wherein R$_8$ is —NH—R$_9$, —O—R$_9$, —CH$_2$—R$_9$, -L-R$_9$, —NH-L-R$_9$, or —O-L-R$_9$, where R$_9$ is a PARP inhibitor, or a derivative or isostere thereof, and where L is a C$_{1-5}$ alkyl linker, optionally comprising an ester or amide linkage.

15. The compound of clause 1, having the structure:

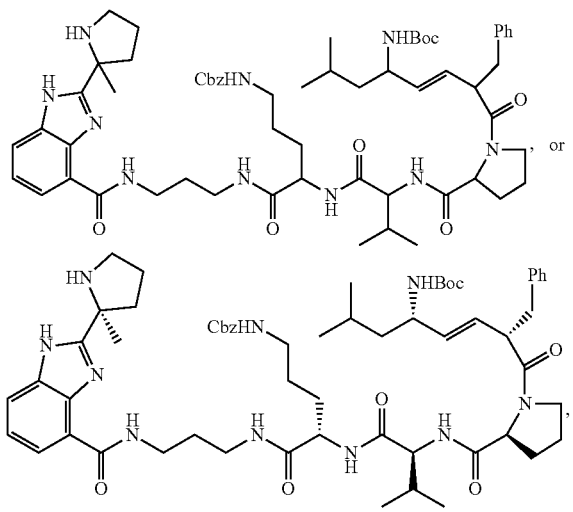

an isostere thereof, or a pharmaceutically acceptable salt or ester thereof.

16. The compound of any of clauses 10-15, wherein the PARP inhibitor is olaparib, veliparib, CEP-8983 (II-methoxy-4,5,6,7-tetrahydro-IH-cyclopenta[a]pyrrolo[3,4-c] carbazole-I,3(2H)-dione) or a prodrug thereof (e.g. CEP-9722), rucaparib, E7016 (10-((4-hydroxypiperidin-I-yl) methyl)chromeno-[4,3,2-de]phthalazin-3(2H)-one), INO-1001 (4-phenoxy-3-pyrrolidin-I-yl-5-sulfamoyl-benzoic acid), niraparib, talazoparib (BMN673), NU1025 (8-hydroxy-2-methylquinazolin-4(3H)-one), 1,5-dihydroiso quinoline, 4-amino-1,8-naphthalimide, 2-nitro-6[5H] phenanthridinone, PD128763, and analogues, isosteres, and derivatives thereof.

17. The compound of any one of clauses 10-16, wherein the PARP inhibitor is veliparib.

18. The compound of any one of clauses 10-17, wherein $R_8$ is:

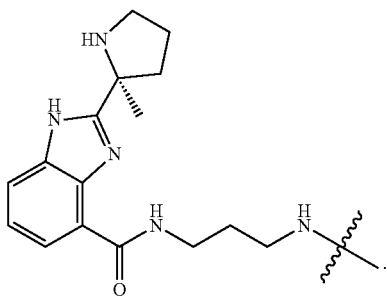 [SMILES: *NCCCNC(=O)c1cccc2[nH]c([C@]3(C)CCCN3)nc12]

19. A composition comprising a first compound according to any one of clauses 1-18, and a pharmaceutically-acceptable excipient.

20. The composition of clause 19, further comprising a chemotherapeutic agent that is different from the first compound.

21. The composition of clause 20, wherein the chemotherapeutic agent is selected from: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyurea-taxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, vinflunine, and combinations thereof, and pharmaceutically acceptable salts or esters thereof.

22. A method of treating a cancer in a patient, comprising administering to a patient an amount of a first compound according to any one of clauses 1-18 effective to sensitize malignant, but not non-malignant, cells of a patient to anti-cancer drugs.

23. The method of clause 23, further comprising administering a radiation therapy to the patient while the first compound is present in the patient.

24. The method of clause 22 or clause 23, further comprising administering a chemotherapeutic agent that differs from the first compound.

25. The method of clause 24, wherein the chemotherapeutic agent is selected from: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyurea-taxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, vinflunine, and combinations thereof, and pharmaceutically acceptable salts or esters thereof.

26. A method of reducing $NAD^+$ depletion and cell death induced by oxidative stress in a cell or a patient, comprising administering to a cell or a patient an amount of a compound according to any one of clauses 1-18 effective to decrease $NAD^+$ depletion in mitochondria of a cell or of a patient.

27. A method of reducing cell death induced by mitochondrial dysfunction and/or damage in a cell or a patient, comprising administering to a cell or a patient an amount of a compound according to any one of clauses 1-18 effective to improve mitochondrial function and reduce mitochondrial damage in a cell or in a patient.

28. A method of reducing energy failure induced by ischemia-reperfusion in a cell or a patient, comprising administering to a cell or a patient an amount of a compound according to any one of clauses 1-18 effective to prevent or reduce ischemia-reperfusion injury in a cell or in a patient.

29. A method of reducing irradiation (IR)-induced cell death and mitochondrial DNA (mtDNA) damage from exposure to ionizing radiation in a patient, comprising administering to a patient an amount of a compound according to any one of clauses 1-18 effective to reduce irradiation (IR)-induced cell death and mitochondrial DNA (mtDNA) damage in a patient.

30. Use of a compound according to any one of clauses 1-18 for the preparation of a medicament for sensitizing malignant, but not non-malignant cells of a patient to anti-cancer drugs.

31. Use of a compound according to any one of clauses 1-18 for the preparation of a medicament for reducing $NAD^+$ depletion and cell death induced by oxidative stress in a cell or a patient.

32. Use of a compound according to any one of clauses 1-18 for the preparation of a medicament for reducing cell death induced by mitochondrial dysfunction and/or damage in a cell or a patient.

33. Use of a compound according to any one of clauses 1-18 for the preparation of a medicament for reducing energy failure induced by ischemia-reperfusion in a cell or a patient.

34. Use of a compound according to any one of clauses 1-18 for the preparation of a medicament for reducing irradiation (IR)-induced cell death and mitochondrial DNA (mtDNA) damage from exposure to ionizing radiation in a patient.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A compound comprising a mitochondria-targeting gramicidin S peptide isostere moiety covalently linked to a PARP inhibitor moiety, an isotere thereof, or a pharmaceutically-acceptable salt or ester thereof, wherein the compound has the structure:

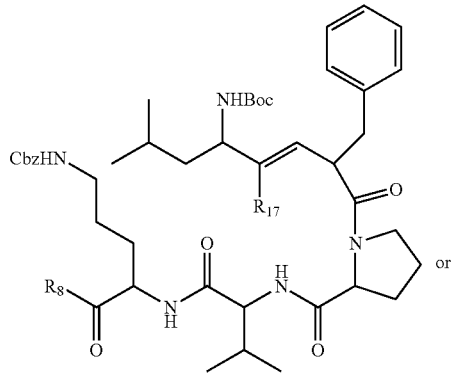

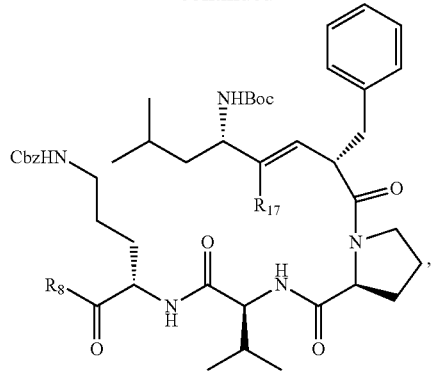

wherein:
$R_8$ is —NH—$R_9$, —O—$R_9$, —$CH_2$—$R_9$, -L-$R_9$, —NH-L-$R_9$, or —O-L-$R_9$, where $R_9$ is a PARP inhibitor moiety and L is a $C_{1-5}$ alkyl linker, optionally comprising an ester or amide linkage; and
$R_{17}$ is methyl or hydrogen.

2. The compound of claim 1, wherein R17 is hydrogen.

3. The compound of claim 1, wherein the PARP inhibitor moiety is an olaparib, veliparib, CEP-8983 (11-methoxy-4, 5,6,7-tetrahydro-1H-cyclopenta[a]pyrrolo[3,4-c]carbazole-1,3(2H)-dione), CEP-9722, rucaparib, E7016 (10-((4-hydroxypiperidin-1-yl)methyl)chromeno-[4,3,2-de] phthalazin-3(2H)-one), INO-1001 (4-phenoxy-3-pyrrolidin-1-yl-5-sulfamoyl-benzoic acid), niraparib, talazoparib (BMN673), NU1025 (8-hydroxy-2-methylquinazolin-4 (3H)-one), 1,5-dihydroiso quinoline, 4-amino-1,8-naphthalimide, 2-nitro-6[5H]phenanthridinone, or PD128763 moiety.

4. The compound of claim 1, wherein the PARP inhibitor is veliparib.

5. The compound of claim 1, having the structure:

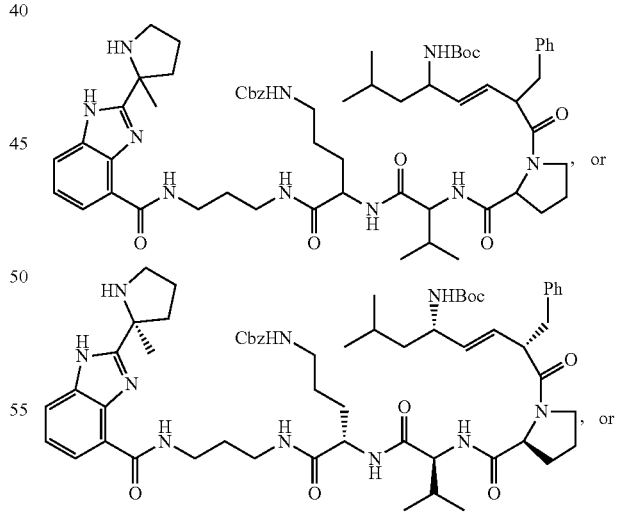

an isostere thereof, or a pharmaceutically acceptable salt thereof.

6. A composition comprising a first compound according to claim 1, and a pharmaceutically-acceptable excipient.

7. The composition of claim 6, further comprising a chemotherapeutic agent that is different from the first compound.

8. The composition of claim 7, wherein the chemotherapeutic agent is selected from: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyurea-taxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, vinflunine, and combinations thereof, and pharmaceutically acceptable salts or esters thereof.

\* \* \* \* \*

UNITED STATES PATENT AND TRADEMARK OFFICE
CERTIFICATE OF CORRECTION

PATENT NO. : 11,759,524 B2
APPLICATION NO. : 17/403182
DATED : September 19, 2023
INVENTOR(S) : Hulya Bayir et al.

It is certified that error appears in the above-identified patent and that said Letters Patent is hereby corrected as shown below:

On the Title Page

Column 2, U.S. Patent Documents, Line 19, after "Niedernhofer" insert -- et al. --

Column 2, Other Publications, Line 4, delete "Cyclopropyi" and insert -- Cyclopropyl --

Column 2, Other Publications, Line 5, delete "Adds"," and insert -- Acids", --

In the Claims

Column 37, Line 48, Claim 1, delete "isotere" and insert -- isostere --

Column 38, Line 24, Claim 2, delete "R17" and insert -- $R_{17}$ --

Column 38, Line 33, Claim 3, delete "dihydroiso quinoline," and insert -- dihydroisoquinoline, --

Column 39, Line 11, Claim 8, delete "decitabine dolastatin," and insert -- decitabine, dolastatin, --

Signed and Sealed this
Thirtieth Day of July, 2024

Katherine Kelly Vidal
*Director of the United States Patent and Trademark Office*